United States Patent
Haeupler et al.

(10) Patent No.: US 10,263,280 B2
(45) Date of Patent: Apr. 16, 2019

(54) 9,10-BIS(1,3-DITHIOL-2-YLIDENE)-9,10-DIHYDROANTHRACENE POLYMERS AND USE THEREOF

(71) Applicants: Bernhard Haeupler, Erlangen (DE); Ulrich Schubert, Jena (DE); Andreas Wild, Weimar (DE)

(72) Inventors: Bernhard Haeupler, Erlangen (DE); Ulrich Schubert, Jena (DE); Andreas Wild, Weimar (DE)

(73) Assignee: Evonik Degussa Gmbh, Essen (DE)

( * ) Notice: Subject to any disclaimer, the term of this patent is extended or adjusted under 35 U.S.C. 154(b) by 217 days.

(21) Appl. No.: 15/129,910

(22) PCT Filed: Mar. 26, 2015

(86) PCT No.: PCT/EP2015/056497
§ 371 (c)(1),
(2) Date: Sep. 28, 2016

(87) PCT Pub. No.: WO2015/144798
PCT Pub. Date: Oct. 1, 2015

(65) Prior Publication Data
US 2017/0179525 A1     Jun. 22, 2017

(30) Foreign Application Priority Data

Mar. 28, 2014 (DE) .................. 10 2014 004 760

(51) Int. Cl.
*C08F 12/30* (2006.01)
*H01M 10/0565* (2010.01)
(Continued)

(52) U.S. Cl.
CPC ...... *H01M 10/0565* (2013.01); *C07D 409/04* (2013.01); *C08F 12/30* (2013.01);
(Continued)

(58) Field of Classification Search
CPC ........ C08F 12/30; C08F 12/34; C08F 134/04; C08G 65/22; H01M 4/608; C07D 409/04
See application file for complete search history.

(56) References Cited

U.S. PATENT DOCUMENTS

| | | |
|---|---|---|
| 2002/0041995 A1 | 4/2002 | Bannai et al. |
| 2002/0041996 A1 | 4/2002 | Morioka et al. |

(Continued)

FOREIGN PATENT DOCUMENTS

| | | |
|---|---|---|
| CA | 2 695 856 A1 | 9/2011 |
| CN | 102683744 A | 9/2012 |

(Continued)

OTHER PUBLICATIONS

German Search Report dated Nov. 14, 2014 in Patent Application No. 10 2014 004 760.1 (Search Report previously filed, submitting English language translation only).

(Continued)

*Primary Examiner* — Cynthia H Kelly
*Assistant Examiner* — Monique M Wills
(74) *Attorney, Agent, or Firm* — Oblon, McClelland, Maier & Neustadt, L.L.P.

(57) ABSTRACT

The problem addressed was that of providing novel polymers which are preparable with a low level of complexity, with the possibility of controlled influence on the physicochemical properties thereof within wide limits in the course of synthesis, and which are usable as active media in electrical charge storage elements for high storage capacity, long lifetime and stable charging/discharging plateaus. 9,10-Bis(1,3-dithiol-2-ylidene)-9,10-dihydroanthracene polymers consisting of an oligomeric or polymeric compound of the general formula I have been found.

(Continued)

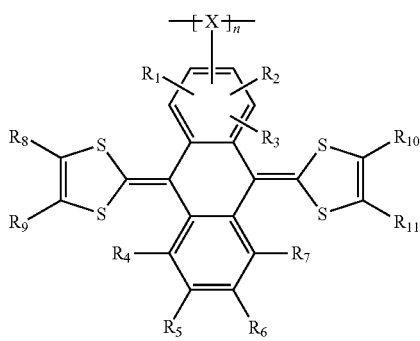

(I)

20 Claims, 3 Drawing Sheets

Figure 1:
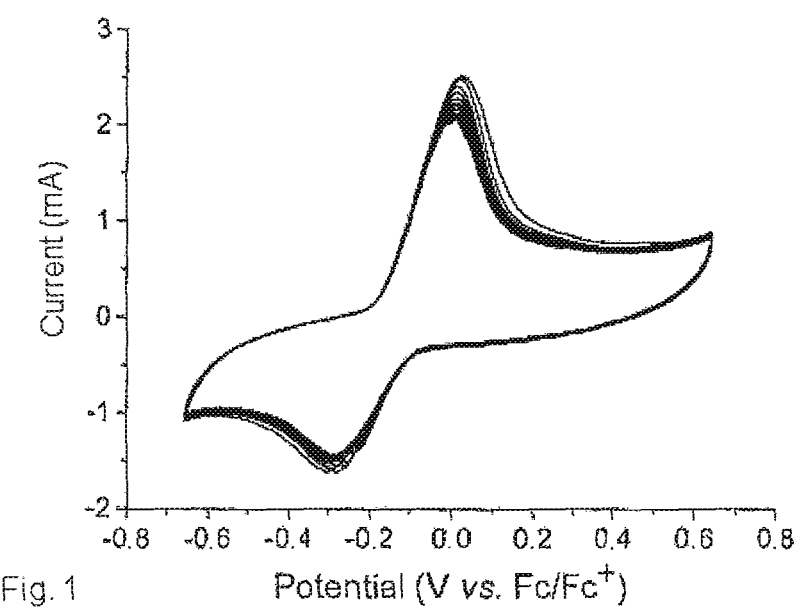

(51) Int. Cl.
| | |
|---|---|
| C08F 12/34 | (2006.01) |
| C08G 65/22 | (2006.01) |
| H01M 4/60 | (2006.01) |
| C07D 409/04 | (2006.01) |
| C08F 134/04 | (2006.01) |

(52) U.S. Cl.
CPC .......... C08F 12/34 (2013.01); C08F 134/04 (2013.01); C08G 65/22 (2013.01); H01M 4/608 (2013.01)

(56) References Cited

U.S. PATENT DOCUMENTS

| | | |
|---|---|---|
| 2003/0062080 A1 | 4/2003 | Satoh et al. |
| 2003/0080322 A1 | 5/2003 | Farrand et al. |
| 2004/0214091 A1 | 10/2004 | Lim et al. |
| 2005/0260500 A1 | 11/2005 | Iwasa et al. |
| 2006/0292452 A1 | 12/2006 | Utsugi et al. |
| 2007/0154815 A1 | 7/2007 | Kawasaki et al. |
| 2008/0051463 A1* | 2/2008 | Gerlach ............ C07C 49/683 514/680 |
| 2010/0167129 A1 | 7/2010 | Wu et al. |
| 2010/0190994 A1* | 7/2010 | Lee .................. C07D 277/22 548/110 |
| 2010/0252112 A1 | 10/2010 | Watson |
| 2010/0255372 A1 | 10/2010 | Suguro et al. |
| 2011/0006294 A1 | 1/2011 | Tanaka et al. |
| 2011/0129730 A1 | 6/2011 | Kasai et al. |
| 2012/0095179 A1 | 4/2012 | Nishide et al. |
| 2012/0100437 A1 | 4/2012 | Nakahara et al. |
| 2012/0171561 A1 | 7/2012 | Iwasa et al. |
| 2012/0189919 A1 | 7/2012 | Abe et al. |
| 2013/0183782 A1 | 7/2013 | Mima |
| 2013/0189571 A1 | 7/2013 | Abouimrane et al. |
| 2013/0209878 A1 | 8/2013 | Nakahara et al. |
| 2014/0038036 A1 | 2/2014 | Nishide et al. |
| 2014/0048786 A1 | 2/2014 | Suzuka et al. |
| 2014/0057167 A1 | 2/2014 | Kasai et al. |
| 2014/0061532 A1 | 3/2014 | Nishide et al. |
| 2014/0079984 A1 | 3/2014 | Kajitani et al. |
| 2014/0087235 A1 | 3/2014 | Kajitani et al. |

FOREIGN PATENT DOCUMENTS

| | | |
|---|---|---|
| CN | 103159919 A | 6/2013 |
| DE | 698 37 190 T2 | 12/2007 |
| EP | 0 924 782 A1 | 6/1999 |
| EP | 1 128 453 A2 | 8/2001 |
| JP | 2001-167885 A | 6/2001 |
| JP | 2002-117852 A | 4/2002 |
| JP | 2002-117854 A | 4/2002 |
| JP | 2002-117855 A | 4/2002 |
| JP | 2004-179169 A | 6/2004 |
| JP | 2004-259618 A | 9/2004 |
| JP | 2005-203341 A | 7/2005 |
| JP | 2005-203342 A | 7/2005 |
| JP | 2005-203343 A | 7/2005 |
| JP | 2006-156314 A | 6/2006 |
| JP | 2006-156315 A | 6/2006 |
| JP | 2008-218326 A | 9/2008 |
| JP | 2008-234909 A | 10/2008 |
| JP | 2009-70827 A | 4/2009 |
| JP | 2009-205918 A | 9/2009 |
| JP | 2009-217992 A | 9/2009 |
| JP | 2009-230951 A | 10/2009 |
| JP | 2009-238612 A | 10/2009 |
| JP | 2009-298873 A | 12/2009 |
| JP | 2010-55923 A | 3/2010 |
| JP | 2010-114042 A | 5/2010 |
| JP | 2010-163551 A | 7/2010 |
| JP | 2010-212152 A | 9/2010 |
| JP | 2010-238403 A | 10/2010 |
| JP | 2011-40311 A | 2/2011 |
| JP | 2011-74317 A | 4/2011 |
| JP | 2011-165433 A | 8/2011 |
| JP | 2011-228050 A | 11/2011 |
| JP | 2011-252106 A | 12/2011 |
| JP | 2012-79639 A | 4/2012 |
| JP | 2012-190545 A | 10/2012 |
| JP | 2012-219109 A | 11/2012 |
| JP | 2012-221574 A | 11/2012 |
| JP | 2012-221575 A | 11/2012 |
| JP | 2013-116949 A | 6/2013 |
| WO | WO 2004/077593 A1 | 9/2004 |
| WO | WO 2005/057715 A1 | 6/2005 |
| WO | WO 2007/141913 A1 | 12/2007 |
| WO | WO 2008/099557 A1 | 8/2008 |
| WO | WO 2009/038125 A1 | 3/2009 |
| WO | WO 2009/145225 A1 | 12/2009 |
| WO | WO 2010/002002 A1 | 1/2010 |
| WO | WO 2010/104002 A1 | 9/2010 |
| WO | WO 201 0/1 4051 | 12/2010 |
| WO | WO 2010/140512 A1 | 12/2010 |
| WO | WO 2011/034117 A1 | 3/2011 |
| WO | WO 2011/068217 A1 | 6/2011 |
| WO | WO 2012/018632 A2 | 2/2012 |
| WO | WO 2012/029556 A1 | 3/2012 |
| WO | WO 2012/120929 A1 | 9/2012 |
| WO | WO 2012/133202 A1 | 10/2012 |
| WO | WO 2012/133204 A1 | 10/2012 |
| WO | WO 2012/153865 A1 | 11/2012 |
| WO | WO 2012/153866 A1 | 11/2012 |
| WO | WO 2013/099567 A1 | 7/2013 |

OTHER PUBLICATIONS

Andreas Wild, et al., "All-Organic Battery Composed of Thianthrene- and TCAQ-Based Polymers" Advanced Energy Materials, XP55324009A, pp. 1-9.

Joaquin Calbo, et al., "Theoretical Insight on Novel Donor-Acceptor exTTF-based Dyes for Dye-Sensitized Solar Cells" Journal of Molecular Modeling, Mar. 2014, pp. 1-10.

Tobias Janoschka, et al., "Storage Devices—Radically Organic" Polymere, 2012, pp. 728-731 (with English translation).

U.S. Appl. No. 14/903,864, filed Jan. 8, 2016, US 2016/0233509 A1, Bernhard Haeupler, et al.

U.S. Appl. No. 15/123,071, filed Sep. 1, 2016, Bernhard Haeupler, et al.,

U.S. Appl. No. 15/247,434, filed Aug. 25, 2016, Bernhard Haeupler, et al.

U.S. Appl. No. 15/247,346, filed Aug. 25, 2016, Bernhard Haeupler, et al.

U.S. Appl. No. 14/903,864, filed May 2, 2016, 2016/0233509, Bernhard Haeupler et al.

German Office Action dated Nov. 14, 2014 in Patent Application No. 10 2014 004 760.1.

(56) References Cited

OTHER PUBLICATIONS

M. Catellani, et al. "Donor-Acceptor 'Double-Cable' Polythiophenes with Tunable Acceptor Content" Thin Solid Films, vol. 451-452, 2004, pp. 2-6.
Beatriz M. Illescas, et al., "Supramolecular Threaded Complexes from Fullerene—Crown Ether and π-Extended TTF Derivatives" Eur. J. Org. Chem. 2007, pp. 5027-5037.
Von H. Hopff, et al., "On 2-Vinylthianthrene and its Polymerization Products" Industrial Chemistry Laboratory of the Swiss Federal Institute of Technology, 1963, pp. 129-138 (with English translation).
Andreas Wild, et al., "All-Organic Battery Composed of Thianthrene- and TCAQ-Based Polymers" Advanced Energy Materials, XP55324009A, 2016, pp. 1-9.
Takakazu Yamamoto, et al., "Oligomeric Poly(phenazine-2,7-diyl) and its Electrochemical Response" Journal of Electroanalytical Chemistry, vol. 460, 1999, pp. 242-244.
Marta C. Diaz, et al., Probing Charge Separation in Structurally Different $C_{60}$/exTTF Ensembles, *The Journal of Organic Chemistry*, 2003, vol. 68, pp. 7711-7721.
International Search Report dated Jun. 25, 2015 in PCT/EP2015/056497 filed Mar. 26, 2015.

\* cited by examiner

9,10-BIS(1,3-DITHIOL-2-YLIDENE)-9,10-DIHYDROANTHRACENE POLYMERS AND USE THEREOF

The invention relates to hitherto unknown 9,10-bis(1,3-dithiol-2-ylidene)-9,10-dihydroanthracene polymers and to the use thereof as active materials in electrical charge storage means such as secondary batteries. In secondary batteries of this kind, the inventive polymers can be used, for example, as active electrode material. These secondary batteries are notable especially for high cell voltages, high power densities and long lifetimes, and also simple and scalable processing and production methods.

The novel 9,10-bis(1,3-dithiol-2-ylidene)-9,10-dihydroanthracene (exTTF) structures of these novel polymers exhibit exceptional electrochemical behaviour. This features a reversible two-electron redox process, as a result of which the electrical charge storage means have a one-stage charging/discharging plateau among other features.

Homo- and copolymers having pendant 9,10-bis(1,3-dithiol-2-ylidene)-9,10-dihydroanthracene units and the derivatives thereof are unknown in the specialist field.

Organic radical batteries are electrochemical cells which use an organic charge storage material as active electrode material for storing electrical charge. These secondary batteries are notable for their exceptional properties, such as fast chargeability, long lifetime, low weight and high flexibility, and also ease of processibility. Some polymeric structures having redox-active units other than the aforementioned novel 9,10-bis(1,3-dithiol-2-ylidene)-9,10-dihydroanthracene polymers, in contrast, have already become known as active electrode materials for charge storage (for example, WO 2012133202 A1, WO 2012133204 A1, WO 2012120929 A1, WO 2012153866 A1, WO 2012153865 A1, JP 2012-221574 A, JP 2012-221575 A, JP 2012-219109 A, JP 2012-079639 A, WO 2012029556 A1, WO 2012153865 A1, JP 2011-252106 A, JP 2011-074317 A, JP 2011-165433 A, WO 2011034117 A1, WO 2010140512 A1, WO 2010104002 A1, JP 2010-238403 A, JP 2010-163551 A, JP 2010-114042 A, WO 2010002002 A1, WO 2009038125 A1, JP 2009-298873 A, WO 2004077593 A1, WO 2009145225 A1, JP 2009-238612 A, JP 2009-230951 A, JP 2009-205918 A, JP 2008-234909 A, JP 2008-218326 A, WO 2008099557 A1, WO 2007141913 A1, US 20020041995 A1, US 20020041995 A1, JP 2002-117852 A, EP 1128453 A2 disclose polymeric compounds having organic nitroxide radicals as active units for charge storage; US 20020041995, JP 2002-117852 A disclose, by way of example, polymeric compounds having organic phenoxy radicals or galvinoxy radicals).

Other known active units for charge storage means are polymeric compounds having quinones (for example JP 2009-217992 A, WO 013/099567 A1, WO 2011/068217 A1), having diones (for example IP 2010-212152 A), and having dicyanodiitnines (for example JP 2012-190545 A, JP 2010-55923 A).

As described, the inventive 9,10-bis(1,3-dithiol-2-ylidene)-9,10-dihydroanthracene polymers are unknown in the specialist field and are therefore not being used as electrical charge storage means.

The theoretical capacity of the already known polymers having redox-active substituents is strictly limited by two factors: firstly by the molar mass of the monomer unit and secondly by the number of electrons involved in the redox reaction of the electrical charge storage. Most organic redox active units have only a one-electron process which is used for charge storage and therefore, as noted above, have a low theoretical capacity because of their comparatively high molar mass.

The use of multi-electron redox processes, as is the case, for example, for quinones or dicyanodiimides, increases the theoretical capacity of the material, but these multi-electron processes are interdependent, and so the redox reactions take place at different potentials and hence several unwanted charging/discharging plateaus arise at different cell voltages in the respective electrical charge storage means. Furthermore, quinones and dicyanodiimides are reduced in the respective redox reaction, and therefore have a low redox potential, leading to a low cell voltage in the electrical charge storage means.

The problem on which the invention is based is therefore that of providing novel polymers which are preparable with a low level of complexity, with the possibility of controlled influence on the physicochemical properties thereof within wide limits in the course of synthesis, and which can be used as active materials in electrical charge storage means with high cell voltage for high storage capacity, long lifetime and a flat charging/discharging plateau.

Novel 9,10-bis(1,3-dithiol-2-ylidene)-9,10-dihydroanthracene polymers consisting of an oligomeric or polymeric compound of the general formula (I) have been found:

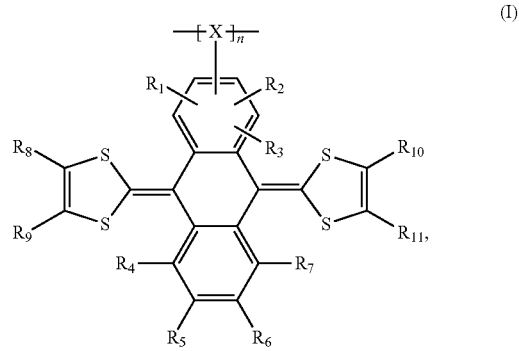

where $R_1$ to $R_7$: may preferably each independently be hydrogen atoms, alkyl groups, alkenyl groups, alkynyl groups, alkoxy groups, alkylthio groups, haloalkyl groups, haloalkoxy groups, cycloalkyl groups, cycloalkoxy groups, aryl groups, heteroaryl groups, aryloxy groups, aralkyl groups, carboxylic acid groups, sulphonic acid groups, amino groups, monoalkylamino groups, dialkylamino groups, nitro groups, cyano groups, hydroxyl groups, alkylcarbonyl groups, alkenylcarbonyl groups, alkynylcarbonyl groups, carboxylic ester groups, carboxamide groups, sulphonic ester groups, thiol groups, halogen atoms or a combination of these groups or atoms, particular preference being given to hydrogen atoms as at least five of the $R_1$ to $R_7$ substituents and to non-hydrogen atoms, preferably halogen atoms, alkyl groups, alkoxy groups, cyano groups and/or nitro groups, as zero to two of the $R_1$ to $R_7$ substituents, $R_8$ to $R_{11}$: may preferably each independently be hydrogen atoms, alkyl groups, alkenyl groups, alkynyl groups, alkoxy groups, alkylthio groups, haloalkyl groups, haloalkoxy groups, cycloalkyl groups, cycloalkoxy groups, aryl groups, heteroaryl groups, aryloxy groups, aralkyl groups, amino groups, monoalkylamino groups, dialkylamino groups, nitro groups, cyano groups, hydroxyl groups, alkylcarbonyl groups, alkenylcarbonyl groups, alkynylcarbonyl groups, carboxylic ester groups, carboxamide groups, sulphonic ester groups, thiol groups, halogen atoms or a combination of these groups or atoms, where the $R_8$ and $R_9$ substituents or the $R_{10}$ and $R_{11}$ substituents may form a further ring consisting of five to seven atoms (the ring may be aromatic, heteroaromatic or nonaromatic; if the ring is nonaromatic, it may consist of various groups, for example alkyl groups, alkenyl groups, alkynyl groups, alkoxy groups, alkylthio groups, haloalkyl groups, haloalkoxy groups, cycloalkyl groups, cycloalkoxy groups, aryl groups, heteroaryl groups, aryloxy groups, aralkyl groups, amino groups, monoalkylamino groups, dialkylamino groups, alkylcarbonyl groups, alkenylcarbonyl groups, alkynylcarbonyl groups, carboxylic ester groups, carboxamide groups, sulphonic ester groups; more preferably, $R_8$ to $R_{11}$ are the same and are each alkyl groups, such as typically methyl groups or ethyl groups, alkylthio groups, such as methylthio groups, or ethylthio groups and thiol groups), X: is an organic group which is formed by polymerization reaction from a group consisting of an organic double bond, an organic triple bond, an oxirane or an aziridine, or is an organic group which is formed by a polymer-analogous reaction, n: is an integer greater than or equal to 2.

The organic X group may preferably have a structure of the following formulae II-XIV:

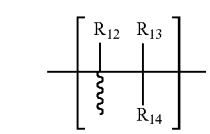  (II)

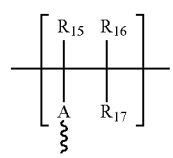  (III)

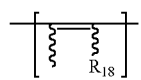  (IV)

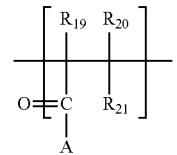  (V)

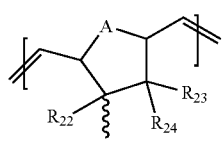  (VI)

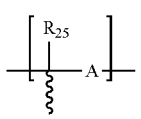  (VII)

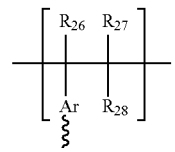  (VIII)

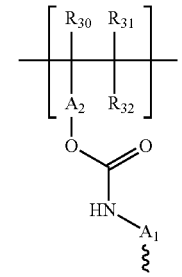  (IX)

(X)

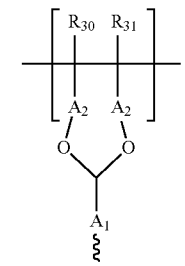

(XI)

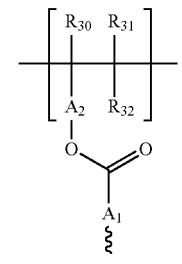  (XII)

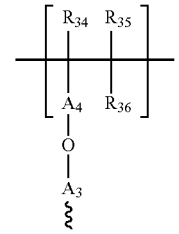

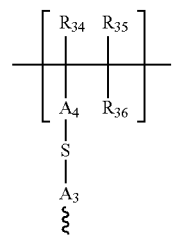  (XIII)

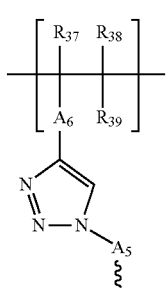

(XIV)

where
$R_{12}$ to $R_{28}$: may preferably each independently be hydrogen atoms, alkyl groups, alkenyl groups, alkynyl groups, alkoxy groups, alkylthio groups, haloalkyl groups, haloalkoxy groups, cycloalkyl groups, cycloalkoxy groups, aryl groups, heteroaryl groups, aryloxy groups, aralkyl groups, carboxylic acid groups, sulphonic acid groups, amino groups, monoalkylamino groups, dialkylamino groups, nitro groups, cyano groups, hydroxyl groups, alkylcarbonyl groups, alkenylcarbonyl groups, alkynylcarbonyl groups, carboxylic ester groups, carboxamide groups, sulphonic ester groups, thiol groups, halogen atoms or a to combination of these groups or atoms, particular preference being given to hydrogen atoms as at least two of the $R_{12}$, to $R_{14}$ substituents and to non-hydrogen atoms, preferably halogen atoms, alkyl groups, alkoxy groups, cyano groups and/or nitro groups, as zero to two of the $R_{12}$ to $R_{14}$ substituents, and/or
   hydrogen atoms as at least two of the $R_{15}$ to $R_{17}$ substituents and to non-hydrogen atoms, preferably halogen atoms, alkyl groups, alkoxy groups, cyano groups and/or nitro groups, as zero to one of the $R_{15}$ to $R_{17}$ substituents, and/or
   a hydrogen atom as $R_{18}$, and/or
   hydrogen atoms as at least two of the $R_{19}$ to $R_{21}$ substituents and to non-hydrogen atoms, preferably halogen atoms, alkyl groups, alkoxy groups, cyano groups and/or nitro groups, as zero to one of the $R_{19}$ to $R_{21}$ substituents, and/or
   hydrogen atoms as at least two of the $R_{22}$ to $R_{24}$ substituents and to non-hydrogen atoms, preferably halogen atoms, alkyl groups, alkoxy groups, cyano groups and/or nitro groups, as zero to one of the $R_{212}$ to $R_{24}$ substituents, and/or
   a hydrogen atom as $R_{25}$, and/or
   hydrogen atoms as at least two of the $R_{26}$ to $R_{28}$ substituents and to non-hydrogen atoms, preferably halogen atoms, alkyl groups, alkoxy groups, cyano groups and/or nitro groups, as zero to one of the $R_{26}$ to $R_{28}$ substituents,
$R_{30}$ to $R_{32}$: may preferably each independently be hydrogen atoms, alkyl groups, alkenyl groups, alkynyl groups, alkoxy groups, alkylthio groups, haloalkyl groups, haloalkoxy groups, cycloalkyl groups, cycloalkoxy groups, aryl groups, heteroaryl groups, aryloxy groups, aralkyl groups, carboxylic acid groups, sulphonic acid groups, amino groups, monoalkylamino groups, dialkylamino groups, nitro groups, cyano groups, hydroxyl groups, alkylcarbonyl groups, alkenylcarbonyl groups, alkynylcarbonyl groups, carboxylic ester groups, carboxamide groups, sulphonic ester groups, thiol groups, halogen atoms or a combination of these groups or atoms, particular preference being given to hydrogen atoms as at least two of the $R_{30}$ to $R_{32}$ substituents and to non-hydrogen atoms, preferably halogen atoms, alkyl groups, alkoxy groups, cyano groups and/or nitro groups, as zero to one of the $R_{30}$ to $R_{32}$ substituents,
$R_{34}$ to $R_{36}$: may preferably each independently be hydrogen atoms, alkyl groups, alkenyl groups, alkynyl groups, alkoxy groups, alkylthio groups, haloalkyl groups, haloalkoxy groups, cycloalkyl groups, cycloalkoxy groups, aryl groups, heteroaryl groups, aryloxy groups, aralkyl groups, carboxylic acid groups, sulphonic acid groups, amino groups, monoalkylamino groups, dialkylamino groups, nitro groups, cyano groups, alkylcarbonyl groups, alkenylcarbonyl groups, alkynylcarbonyl groups, carboxylic ester groups, carboxamide groups, sulphonic ester groups, halogen atoms or a combination of these groups or atoms, particular preference being given to hydrogen atoms as at least two of the $R_{34}$ to $R_{36}$ substituents and to non-hydrogen atoms, preferably halogen atoms, alkyl groups, alkoxy groups, cyano groups and/or nitro groups, as zero to one of the $R_{34}$ to $R_{36}$ substituents,
$R_{37}$ to $R_{39}$: may preferably each independently be hydrogen atoms, alkyl groups, alkenyl groups, alkoxy groups, alkylthio groups, haloalkyl groups, haloalkoxy groups, cycloalkyl groups, cycloalkoxy groups, aryl groups, heteroaryl groups, aryloxy groups, aralkyl groups, carboxylic acid groups, sulphonic acid groups, amino groups, monoalkylamino groups, dialkylamino groups, nitro groups, cyano groups, hydroxyl groups, alkylcarbonyl groups, alkenylcarbonyl groups, alkynylcarbonyl groups, carboxylic ester groups, carboxamide groups, sulphonic ester groups, thiol groups, halogen atoms or a combination of these groups or atoms, particular preference being given to hydrogen atoms as at least two of the $R_{37}$ to $R_{39}$ substituents and to non-hydrogen atoms, preferably halogen atoms, alkyl groups, alkoxy groups, cyano groups and/or nitro groups, as zero to one of the $R_{37}$ to $R_{39}$ substituents,
A: is an oxygen atom, a sulphur atom or an —$N(R_{33})$— group, where $R_{33}$ is preferably a hydrogen atom, an alkyl group, an alkenyl group, an alkynyl group, an alkoxy group, an alkylthio group, a haloalkyl group, a haloalkoxy group, a cycloalkyl group, a cycloalkoxy group, an aryl group, a heteroaryl group, an aryloxy group, an aralkyl group, a carboxylic acid group, a sulphonic acid group, a nitro group, an alkylcarbonyl group, an alkenylcarbonyl group, an alkynylcarbonyl group, a carboxylic ester group, a carboxamide group, a sulphonic ester group, particular preference being given to an oxygen atom as A,
$A_1$ and $A_2$: are preferably each independently a covalent bond, an alkyl group, an alkenyl group, an alkynyl group, an alkoxy group, an alkylthio group, a haloalkyl group, a haloalkoxy group, a cycloalkyl group, a cycloalkoxy group, an aryl group, a heteroaryl group, an aryloxy group, an aralkyl group, a monoalkylamino group, a dialkylamino group, an alkylcarbonyl group, an alkenylcarbonyl group, an alkynylcarbonyl group, a carboxylic ester group, a carboxamide group, a sulphonic ester group, particular preference being given to a covalent bond or an alkyl group as $A_1$ and $A_2$)
$A_3$ and $A_4$: may preferably each independently be a covalent bond, an alkyl group, an alkenyl group, an alkynyl group, an alkoxy group, an alkylthio group, a cycloalkyl group, a cycloalkoxy group, an aryl group, a heteroaryl group, an aryloxy group, an aralkyl group, a dialkylamino group, an alkylcarbonyl group, an alkenylcarbonyl group, an alkynylcarbonyl group, a carboxylic ester group, a carboxamide group, a sulphonic ester group, particular preference being given to a covalent bond or an alkyl group as $A_1$ and $A_2$, $A_5$ and $A_6$: may preferably each independently be a covalent bond, an alkyl group, an alkenyl group, an alkoxy group, an alkylthio group, a haloalkyl group, a haloalkoxy group, a cycloalkyl group, a cycloalkoxy group, an aryl group, a heteroaryl group, an aryloxy group, an aralkyl group, a monoalkylamino group, a dialkylamino group, an alkylcarbonyl group, an alkenylcarbonyl group, an alkynylcarbonyl group, a carboxylic ester group, a carboxamide group, a sulphonic ester group, particular preference being given to a covalent bond, an aryl group or an alkyl group as $A_5$ and $A_6$, Ar: is an independently substituted cycloalkyl group, cycloalkoxy group, aryl group, heteroaryl group, aryloxy group, aralkyl group.

Novel polymers containing 9,10-bis(1,3-dithiol-2-ylidene)-9,10-dihydroanthracene units as the pendant group on the polymer backbone have been synthesized. These polymers have excellent properties, especially as redox active electrode material in cathodes for secondary electrical charge storage means. The dependent claims specify advantageous possible uses of the inventive 9,10-bis(1,3-dithiol-2-ylidene)-9,10-dihydroanthracene polymers.

These novel polymers can be prepared in a simple and uncomplicated manner, and from readily obtainable starting materials. No further monomer is needed for the polymerization, and the polymerization does not require any costly metal catalysts; instead, it is possible to use simple polymerization processes as the production method. At the same time, it is possible to obtain polymers having a high molar mass and low polydispersity index in very high yields. The introduction of polymerizable groups of low molar mass makes it possible to keep the molar mass of the monomer low and to maximize the theoretical capacity of the secondary electrical charge storage means, in addition, the redox active groups in these polymers are not conjugated to one another; as a consequence, the electrical charge storage means has a flat charging/discharging plateau. These materials differ from the prior art by a two-electron redox reaction which leads to said flat charging/discharging plateau, combined with simultaneously high capacity and long lifetime in the component.

In the description which follows, n is defined as normal, i as iso, s as secondary, t as tertiary, c as cyclo, m as meta, p as para and o as ortho.

In this specification, an alkyl group may be either branched or unbranched. An alkyl group typically consists of one up to thirty carbon atoms, preferably of one up to twenty carbon atoms. Examples of an alkyl group are: methyl group, ethyl group, propyl group, isopropyl group, n-butyl group, sec-butyl group, t-butyl group, pentyl group, n-hexyl group, n-heptyl group, 2-ethylhexyl group, n-octyl group, n-nonyl group, n-decyl group, n-undecyl group, n-dodecyl group, n-tridecyl group, n-tetradecyl group, n-pentadecyl group, n-hexadecyl group, n-heptadecyl group, n-octadecyl group, n-nonadecyl group or eicosyl group. Particular preference is given to alkyl groups having one to six carbon atoms.

In this specification, an alkenyl group may be either branched or unbranched. An alkenyl group typically consists of one up to thirty carbon atoms, preferably of one up to twenty carbon atoms. Alkenyl groups typically have one unsaturated ethenylic double bond; the remaining proportion of the alkenyl group is saturated. Two or more ethenylic unsaturated double bonds are possible but not preferred. The unsaturated ethenylic double bond is more preferably at the alpha position in the alkenyl group. Examples of an alkenyl group are: vinyl group, allyl group, propenyl group, isopropenyl group, n-butenyl group, sec-butenyl group, pentenyl group, n-hexenyl group, n-heptenyl group, 2-ethylhexenyl group, n-octenyl group, n-nonenyl group, n-decenyl group, n-undecenyl group, n-dodecenyl group, n-tridecenyl group, n-tetradecenyl group, n-pentadecenyl group, n-hexadecenyl group, n-heptadecenyl group, n-octadecenyl group, n-nonadecenyl group or eicoseny group. Preference is given to alkenyl groups having two to three carbon atoms; particular preference is given to vinyl groups and allyl groups.

In this specification, an alkynyl group may be either branched or unbranched. An alkynyl group typically consists of two up to thirty carbon atoms, preferably of one to twenty carbon atoms. Alkynyl groups typically have one unsaturated ethynylic triple bond; the remaining proportion of the alkynyl group is saturated. Two or more ethynylic unsaturated triple bonds are possible but not preferred. The unsaturated ethynylic double bond is more preferably at the alpha position in the alkynyl group. Examples of an alkynyl group are: ethynyl group, propynyl group, butynyl group, pentynyl group, n-hexynyl group, n-heptynyl group, 2-ethylhexynyl group, n-octynyl group, n-nonynyl group, n-decynyl group, n-undecynyl group, n-dodecynyl group, n-tridecynyl group, n-tetradecynyl group, n-pentadecynyl group, n-hexadecynyl group, n-heptadecynyl group, n-octadecynyl group, n-nonadecynyl group or eicosynyl group. Preference is given to alkynyl groups having two carbon atoms.

In this specification, an alkylthio group may be either branched or unbranched. An alkylthio group typically consists of one up to thirty carbon atoms and one or more sulphur atoms bonded covalently to two carbon atoms in the chain, preferably of one to twenty carbon atoms and one sulphur atom. Examples of an alkylthio group are: methylthio group, ethylthio group, n-propylthio group, i-propylthio group, n-butylthio group, s-butylthio group, t-butylthio group, n-pentylthio group, 1-methylbutylthio group, 2-methylbutylthio group, 3-methylbutylthio group, 1,1-dimethylpropylthio group, 2,2-dimethylpropylthio group, n-hexylthio group, 1-methylpentylthio group, 2-methylpentylthio group, 1,1-dimethylbutylthio group, 1-ethylbutylthio group, 1,1,2-trimethylpropylthio group, n-heptylthio group, n-octylthio group, 2-ethylhexylthio group, n-nonylthio group, n-decylthio group, n-dodecylthio group.

In this specification, a monoalkylamino group may be either branched or unbranched. A monoalkylamino group typically consists of one up to thirty carbon atoms and one or more nitrogen atoms bonded covalently to two carbon atoms in the chain, preferably of one to twenty carbon atoms and one nitrogen atom. Examples of a monoalkylamino group are: methylamino group, ethylamino group, n-propylamino group, i-propylamino group, c-propylamino group, n-butylamino group, i-butylamino group, s-butylamino group, t-butylamino group, c-butylamino group, 1-methyl-c-propylamino group, 2-methyl-c-propylamino group, n-pentylamino group, 1-methyl-n-butylamino group, 2-methyl-n-butylamino group, 3-methyl-n-butylamino group, 1,1-dimethyl-n-propylamino group, 1,2-dimethyl-n-propylamino group, 2,2-dimethyl-n-propylamino group, 1-ethyl-n-propylamino group, c-pentylamino group, 1-methyl-c-butylamino group, 2-methyl-c-butylamino group, 3-methyl-c-butylamino group, 1,2-dimethyl-c-propylamino group, 2,3-dimethyl-c-propylamino group, 1-ethyl-c-propylamino group, 2-ethyl-c-propylamino group, n-hexylamino group, 1-methyl-n-pentylamino group, 2-methyl-n-pentylamino group, 3-methyl-n-pentylamino group, 4-methyl-n-pentylamino group, 1,1-dimethyl-n-butylamino group, 1,2-dimethyl-n-butylamino group, 1,3-dimethyl-n-butylamino group, 2,2-dimethyl-n-butylamino group, 2,3-dimethyl-n-butylamino group, 3,3-dimethyl-n-butylamino group, 1-ethyl-n-butylamino group, 2-ethyl-n-butylamino group, 1,1,2-trimethyl-n-propylamino group, 1,2,2-trimethyl-n-propylamino group, 1-ethyl-1-methyl-n-propylamino group, 1-ethyl-2-methyl-n-propylamino group, c-hexylamino group, 1-methyl-c-pentylamino group, 2-methyl-c-pentylamino group, 3-methyl-c-pentylamino group, 1-ethyl-c-butylamino group, 2-ethyl-c-butylamino group, 3-ethyl-c-butylamino group, 1,2-dimethyl-c-butylamino group, 1,3-dimethyl-c-butylamino group, 2,2-dimethyl-c-butylamino group, 2,3-dimethyl-c-butylamino group, 2,4-dimethyl-c-butylamino group, 3,3-dimethyl-c-butylamino group, 1-n-propyl-c-propylamino group, 2-n-propyl-c-propylamino group, 1-i-propyl-c-propylamino group, 2-i-propyl-c-propylamino group, 1,2,2-trimethyl-c-propylamino group, 1,2,3-trimethyl-c-propylamino group, 2,2,3-trimethyl-c-propylamino group, 1-ethyl-2-methyl-c-propylamino group, 2-ethyl-1-methyl-c-propylamino group, 2-ethyl-2-methyl-c-propylamino group, 2-ethyl-3-methyl-c-propylamino group.

In this specification, a dialkylamino group may be either branched or unbranched. A dialkylamino group typically consists of one up to thirty carbon atoms and one or more nitrogen atoms bonded covalently to three carbon atoms in the chain, preferably of one to twenty carbon atoms and one nitrogen atom. Examples of a dialkylamino group are: di-i-propylamino group, di-c-propylamino group, di-n-butylamino group, di-i-butylamino group, di-s-butylamino group, di-t-butylamino group, di-c-butylamino group, di(1-methyl-c-propyl)amino group, di(2-methyl-c-propyl)amino group, di-n-pentylamino group, di(1-methyl-n-butyl)amino group, di(2-methyl-n-butyl)amino group, di(3-methyl-n-butypamino group, di(1,1-dimethyl-n-propyl)amino group, di(1,2-dimethyl-n-propyl)amino group, di(2,2-dimethyl-n-propyl)amino group, di(1-ethyl-n-propyl)amino group, di-c-pentylamino group, di(1-methyl-c-butypamino group, di(2-methyl-c-butyl)amino group, di(3-methyl-c-butyl)amino group, di(1,2-dimethyl-c-propyl)amino group, di(2,3-dimethyl-c-propyl)amino group, di(1-ethyl-c-propyl)amino group, di(2-ethyl-c-propyl)amino group, di-n-hexylamino group, di(1-methyl-n-pentypamino group, di(2-methyl-n-pentyl)amino group, di(3-methyl-n-pentypamino group, di(4-methyl-n-pentyl)amino group, di(1,1-dimethyl-n-butyl)amino group, di(1,2-dimethyl-n-butyl)amino group, di(1,3-dimethyl-n-butyl)amino group.

In this specification, a haloalkyl group may be either branched or unbranched. A haloalkyl group typically consists of one up to thirty carbon atoms which may in turn each independently be substituted by one or more halogen atoms, preferably of one to twenty carbon atoms. Examples of halogen atoms are the fluorine atom, chlorine atom, bromine atom and iodine atom. Preference is given to the fluorine atom and the chlorine atom.

Examples of a haloalkyl group are: difluoromethoxy group, trifluorotnethoxy group, bromodifluorotnethoxy group, 2-chloroethoxy group, 2-bromoethoxy group, 1,1-difluoroethoxy group, 2,2,2-trifluoroethoxy group, 1,1,2,2-tetrafluoroethoxy group, 2-chloro-1,1,2-trifluoroethoxy group, pentafluoroethoxy group, 3-bromopropoxy group, 2,2,3,3-tetrafluoropropoxy group, 1,1,2,3,3,3-hexafluoropropoxy group, 1,1,1,3,3,3-hexafluoropropoxy group, 3-bromo-2-methylpropoxy group, 4-bromobutoxy group, perfluoropentyloxy group.

In this specification, a haloalkoxy group may be either branched or unbranched. A haloalkoxy group typically consists of an oxygen atom with a chain consisting of one up to thirty carbon atoms covalently bonded thereto, which may be either branched or unbranched, and wherein the carbon atoms may in turn each independently be substituted by one or more halogen atoms. This chain preferably consists of one to twenty carbon atoms. Examples of halogen atoms are the fluorine atom, chlorine atom, bromine atom and iodine atom. Preference is given to the fluorine atom and the chlorine atom. Examples of a haloalkoxy group are: difluoromethoxy group, trifluoromethoxy group, bromoditluoromethoxy group, 2-chloroethoxy group, 2-bromoethoxy group, 1,1-difluoroethoxy group, 2,2,2-trifluoroethoxy group, 1,1,2,2-tetrafluoroethoxy group, 2-chloro-1,1,2-trifluoroethoxy group, pentafluoroethoxy group, 3-bromopropoxy group, 2,2,3,3-tetrafluoropropoxy group, 1,1,2,3,3,3-hexafluoropropoxy group, 1,1,1,3,3,3-hexafluoropropoxy group, 3-bromo-2-methylpropoxy group, 4-bromobutoxy group, perfluoropentoxy group.

An alkylcarbonyl group in this specification typically consists of a carbonyl carbon with an alkyl group consisting of one up to thirty carbon atoms bonded covalently thereto, which may be either branched or unbranched. This chain preferably consists of one to twenty carbon atoms. Examples of an alkylcarbonyl group are: methylcarbonyl group, ethylcarbonyl group, n-propylcarbonyl group, i-propylcarbonyl group, c-propylcarbonyl group, n-butylcarbonyl group, i-butylcarbonyl group, s-butylcarbonyl group, t-butylcarbonyl group, c-butylcarbonyl group, 1-methyl-c-propylcarbonyl group, 2-methyl-c-propylcarbonyl group, n-pentylcarbonyl group, 1-methyl-n-butylcarbonyl group, 2-methyl-n-butylcarbonyl group, 3-methyl-n-butylcarbonyl group, 1,1-dimethyl-n-propylcarbonyl group, 1,2-dimethyl-n-propylcarbonyl group, 2,2-dimethyl-n-propylcarbonyl group, 1-ethyl-n-propylcarbonyl group, c-pentylcarbonyl group, 1-methyl-c-butylcarbonyl group, 2-methyl-c-butylcarbonyl group, 3-methyl-c-butylcarbonyl group, 1,2-dimethyl-c-propylcarbonyl group, 2,3-dimethyl-c-propylcarbonyl group, 1-ethyl-c-propylcarbonyl group, 2-ethyl-c-propylcarbonyl group, n-hexylcarbonyl group, 1-methyl-n-pentylcarbonyl group, 2-methyl-n-pentylcarbonyl group, 3-methyl-n-pentylcarbonyl group, 4-methyl-n-pentylcarbonyl group, 1,1-dimethyl-n-butylcarbonyl group, 1,2-dimethyl-n-butylcarbonyl group, 1,3-dimethyl-n-butylcarbonyl group, 2,2-dimethyl-n-butylcarbonyl group, 2,3-dimethyl-n-butylcarbonyl group, 3,3-dimethyl-n-butylcarbonyl group, 1-ethyl-n-butylcarbonyl group, 2-ethyl-n-butylcarbonyl group.

An alkenylcarbonyl group in this specification typically consists of a carbonyl carbon with an alkenyl group consisting of one up to thirty carbon atoms bonded covalently thereto, which may be either branched or unbranched. This chain preferably consists of one to twenty carbon atoms. Examples of an alkenylcarbonyl group are: ethenylcarbonyl group, 1-propenylcarbonyl group, 2-propenylcarbonyl group, 1-methyl-1-ethenylcarbonyl group, 1-butenylcarbonyl group, 2-butenylcarbonyl group, 3-butenylcarbonyl group, 2-methyl-1-propenylcarbonyl group, 2-methyl-2-propenylcarbonyl group, 1-ethylethenylcarbonyl group, 1-methyl-1-propenylcarbonyl group, 1-methyl-2-propenylcarbonyl group, 1-pentenylcarbonyl group, 2-pentenylcarbonyl group, 3-pentenylcarbonyl group, 4-pentenylcarbonyl group, 1-n-propylethenylcarbonyl group, 1-methyl-1-butenylcarbonyl group, 1-methyl-2-butenylcarbonyl group, 1-methyl-3-butenylcarbonyl group, 2-ethyl-2-propenylcarbonyl group, 2-methyl-1-butenylcarbonyl group, 2-methyl-2-butenylcarbonyl group, 2-methyl-3-butenylcarbonyl group, 3-methyl-1-butenylcarbonyl group, 3-methyl-2-butenylcarbonyl group, 3-methyl-3-butenylcarbonyl group, 1,1-dimethyl-2-propenylcarbonyl group, 1-i-propylethenylcarbonyl group, 1,2-dimethyl-1-propenylcarbonyl group, 1,2-dimethyl-2-propenylcarbonyl group, 1-c-pentenylcarbonyl group, 2-c-pentenylcarbonyl group, 3-c-pentenylcarbonyl group, 1-hexenylcarbonyl group, 2-hexenylcarbonyl group, 3-hexenylcarbonyl group, 4-hexenylcarbonyl group, 5-hexenylcarbonyl group, 1-methyl-1-pentenylcarbonyl group, 1-methyl-2-pentenylcarbonyl group, 1-methyl-3-pentenylcarbonyl group, 1-methyl-4-pentenylcarbonyl group, 1-n-butylethenylcarbonyl group, 2-methyl-1-pentenylcarbonyl group, 2-methyl-2-pentenylcarbonyl group, 2-methyl-3-pentenylcarbonyl group, 2-methyl-4-pentenylcarbonyl group, 2-n-propyl-2-propenylcarbonyl group, 3-methyl-1-pentenylcarbonyl group, 3-methyl-2-pentenylcarbonyl group.

An alkynylcarbonyl group in this specification typically consists of a carbonyl carbon with an alkynyl group consisting of one up to thirty carbon atoms bonded covalently thereto, which may be either branched or unbranched. This chain preferably consists of one to twenty carbon atoms. Examples of an alkynylcarbonyl group are: ethynylcarbonyl group, 1-propynylcarbonyl group, 2-propynylcarbonyl group, 1-butynylcarbonyl group, 2-butynylcarbonyl group, 3-butynylcarbonyl group, 1-methyl-2-propynylcarbonyl group, 1-group, 2-pentynylcarbonyl group, 3-pentynylcarbonyl group, 4-pentynylcarbonyl group, 1-methyl-2-butynylcarbonyl group, 1-methyl-3-butynylcarbonyl group, 2-methyl-3-butynylcarbonyl group, 3-methyl-1-butynylcarbonyl group, 1,1-dimethyl-2-propynyl carbonyl group, 2-ethyl-2-propynylcarbonyl group, 1-hexynylcarbonyl group, 2-hexynylcarbonyl group, 3-hexynylcarbonyl group, 4-hexynylcarbonyl group, 5-hexynylcarbonyl group, 1-methyl-2-pentynylcarbonyl group, 1-methyl-3-pentynylcarbonyl group, 1-methyl-4-pentynylcarbonyl group, 2-methyl-3-pentyny carbonyl group, 2-methyl-4-pentynylcarbonyl group, 3-methyl-1-pentynylcarbonyl group, 3-methyl-4-pentynylcarbonyl group, 4-methyl-1-pentynylcarbonyl group, 4-methyl-2-pentynylcarbonyl group, 1,1-dimethyl-2-butynylcarbonyl group, 1,1-dimethyl-3-butynylcarbonyl group, 1,2-dimethyl-3-butynylcarbonyl group, 2,2-dimethyl-3-butynylcarbonyl group, 3,3-dimethyl-1-butynylcathonyl group, 1-ethyl-2-butynylcarbonyl group, 1-ethyl-3-butynylcarbonyl group.

An alkylcarboxylic ester group in this specification typically consists of a carboxylic ester with an alkyl group consisting of one up to thirty carbon atoms bonded covalently thereto, which may be either branched or unbranched. This chain preferably consists of one to twenty carbon atoms. Examples of an alkylcarboxylic ester group are: methylcarboxylic ester group, ethylcarboxylic ester group, n-propylcarboxylic ester group, i-propylcarboxylic ester group, c-propylcarboxylic ester group, n-butylcarboxylic ester group, i-butylcarboxylic ester group, s-butylcarboxylic ester group, t-butylcarboxylic ester group, c-butylcarboxylic ester group, 1-methyl-c-propylcarboxylic ester group, 2-methyl-c-propylcarboxylic ester group, n-pentylcarboxylic ester group, 1-methyl-n-butylcarboxylic ester group, 2-methyl-n-butylcarboxylic ester group, 3-methyl-n-butylcarboxylic ester group, 1,1-dimethyl-n-propylcarboxylic ester group, 1,2-dimethyl-n-propylcarboxylic ester group, 2,2-dimethyl-n-propylcarboxylic ester group, 1-ethyl-n-propylcarboxylic ester group, c-pentylcarboxylic ester group, 1-methyl-c-butylcarboxylic ester group, 2-methyl-c-butylcarboxylic ester group, 3-methyl-c-butylcarboxylic ester group, 1,2-dimethyl-c-propylcarboxylic ester group, 2,3-dimethyl-c-propylcarboxylic ester group, 1-ethyl-c-propylcarboxylic ester group, 2-ethyl-c-propylcarboxylic ester group, n-hexylcarboxylic ester group, 1-methyl-n-pentylcarboxylic ester group, 2-methyl-n-pentylcarboxylic ester group, 3-methyl-n-pentylcarboxylic ester group, 4-methyl-n-pentylcarboxylic ester group, 1,1-dimethyl-n-butylcarboxylic ester group, 1,2-dimethyl-n-butylcarboxylic ester group, 1,3-dimethyl-n-butylcarboxylic ester group, 2,2-dimethyl-n-butylcarboxylic ester group, 2,3-dimethyl-n-butylcarboxylic ester group, 3,3-dimethyl-n-butylcarboxylic ester group, 1-ethyl-n-butylcarboxylic ester group, 2-ethyl-n-butylcarboxylic ester group.

An alkenylcarboxylic ester group in this specification typically consists of a carboxylic ester with an alkenyl group consisting of one up to thirty carbon atoms bonded covalently thereto, which may be either branched or unbranched. This chain preferably consists of one to twenty carbon atoms. Examples of an alkenylcarboxylic ester group are: ethenylcarboxylic ester group, 1-propenylcarboxylic ester group, 2-propenylcarboxylic ester group, 1-methyl-1-ethenylcarboxylic ester group, 1-butenylcarboxylic ester group, 2-butenylcarboxylic ester group, 3-butenylcarboxylic ester group, 2-methyl-1-propenylcarboxylic ester group, 2-methyl-2-propenylcarboxylic ester group, 1-ethylethenylcarboxylic ester group, 1-methyl-1-propenylcarboxylic ester group, 1-methyl-2-propenylcarboxylic ester group, 1-pentenylcarboxylic ester group, 2-pentenylcarboxylic ester group, 3-pentenylcarboxylic ester group, 4-pentenylcarboxylic ester group, 1-n-propylethenylcarboxylic ester group, 1-methyl-1-butenylcarboxylic ester group, 1-methyl-2-butenylcarboxylic ester group, 1-methyl-3-butenylcarboxylic ester group, 2-ethyl-2-propenylcarboxylic ester group, 2-methyl-1-butenylcarboxylic ester group, 2-methyl-2-butenylcarboxylic ester group, 2-methyl-3-butenylcarboxylic ester group, 3-methyl-1-butenylcarboxylic ester group, 3-methyl-2-butenylcarboxylic ester group, 3-methyl-3-butenylcarboxylic ester group, 1,1-dimethyl-2-propenylcarboxylic ester group, 1-i-propylethenylcarboxylic ester group, 1,2-dimethyl-1-propenylcarboxylic ester group, 1,2-dimethyl-2-propenylcarboxylic ester group, 1-c-pentenylcarboxylic ester group, 2-c-pentenylcarboxylic ester group, 3-c-pentenylcarboxylic ester group, 1-hexenylcarboxylic ester group, 2-hexenylcarboxylic ester group, 3-hexenylcarboxylic ester group, 4-hexenylcarboxylic ester group, 5-hexenylcarboxylic ester group, 1-methyl-1-pentenylcarboxylic ester group, 1-methyl-2-pentenylcarboxylic ester group, 1-methyl-3-pentenylcarboxylic ester group, 1-methyl-4-pentenylcarboxylic ester group, 1-n-butylethenylcarboxylic ester group, 2-methyl-1-pentenylcarboxylic ester group, 2-methyl-2-pentenylcarboxylic ester group, 2-methyl-3-pentenylcarboxylic ester group, 2-methyl-4-pentenylcarboxylic ester group, 2-n-propyl-2-propenylcarboxylic ester group, 3-methyl-1-pentenylcarboxylic ester group, 3-methyl-2-pentenylcarboxylic ester group.

An alkynylcarboxylic ester group in this specification typically consists of a carboxylic ester with an alkynyl group consisting of one up to thirty carbon atoms bonded covalently thereto, which may be either branched or unbranched. This chain preferably consists of one to twenty carbon atoms. Examples of an alkynylcarboxylic ester group are: ethynylcarboxylic ester group, 1-propynylcarboxylic ester group, 2-propynylcarboxylic ester group, 1-butynylcarboxylic ester group, 2-butynylcarboxylic ester group, 3-butynylcarboxylic ester group, 1-methyl-2-propynylcarboxylic ester group, 1-pentynylcarboxylic ester group, 2-pentynylcarboxylic ester group, 3-pentynylcarboxylic ester group, 4-pentynylcarboxylic ester group, 1-methyl-2-butynylcarboxylic ester group, 1-methyl-3-butynylcarboxylic ester group, 2-methyl-3-butynylcarboxylic ester group, 3-methyl-1-butymylcarboxylic ester group, 1,1-dimethyl-2-propynylcarboxylic ester group, 2-ethyl-2-propynylcarboxylic ester group, 1-hexynylcarboxylic ester group, 2-hexynylcarboxylic ester group, 3-hexynylcarboxylic ester group, 4-hexynylcarboxylic ester group, 5-hexynylcarboxylic ester group, 1-methyl-2-pentynylcarboxylic ester group, 1-methyl-3-pentynylcarboxylic ester group, 1-methyl-4-pentynylcarboxylic ester group, 2-methyl-3-pentynylcarboxylic ester group, 2-methyl-4-pentynylcarboxylic ester group, 3-methyl-1-pentynylcarboxylic ester group, 3-methyl-4-pentynylcarboxylic ester group, 4-methyl-1-pentynylcarboxylic ester group, 4-methyl-2-pentynylcarboxylic ester group, 1,1-dimethyl-2-butynylcarboxylic ester group, 1,1-dimethyl-3-butynylcarboxylic ester group, 1,2-dimethyl-3-butynylcarboxylic ester group, 2,2-dimethyl-3-butynylcarboxylic ester group, 3,3-dimethyl-1-butynylcarboxylic ester group, 1-ethyl-2-butynylcarboxylic ester group, 1-ethyl-3-butynylcarboxylic ester group.

In this specification, an alkoxy group may consist of an alkyl unit which may be either branched or unbranched. An alkoxy group typically consists of one to thirty carbon atoms, preferably of one to twenty carbon atoms. Examples of an alkoxy group are: methoxy group, ethoxy group, isopropoxy group, n-butoxy group, sec-butoxy group, tert-butoxy group, pentyloxy group, n-hexyloxy group, n-heptyloxy group, 2-ethylhexyloxy group, n-octyloxy group, n-nonyloxy group, n-decyloxy group, n-tridecyloxy group, n-tetradecyloxy group, n-pentadecyloxy group, n-hexadecyloxy group, n-octadecyloxy group or eicosyloxy group. Preference is given to alkoxy groups having one up to six carbon atoms in the alkyl unit.

A cycloalkyl group as described in this specification is typically a cyclic group consisting of five, six or seven carbon atoms, each of which may independently be substituted. Examples of substituents are alkyl groups, or two alkyl groups which, together with the ring carbons to which they are bonded, form a further ring. One example of a cycloalkyl group is a cyclohexyl group.

A cycloalkoxy group as described in this specification is typically a cyclic group consisting of five, six or seven carbon atoms, of which at least one is bonded covalently to an oxygen atom. These ring carbon atoms may each independently be substituted, for example by alkyl groups, or two alkyl groups which, together with the ring carbons to which they are bonded, form a further ring. One example of a cycloalkoxy group is a cyclohexyloxy group.

An aryl group as described in this specification is typically a cyclic aromatic group consisting of five to ten carbon atoms, each of which may independently be substituted. Examples of substituents are alkyl groups, or two alkyl groups which, together with the ring carbons to which they are bonded, form a further ring. Examples of an aryl group are phenyl group, o-biphenylyl group, m-biphenylyl group, p-biphenylyl group, 1-anthryl group, 2-anthryl group, 9-anthryl group, 1-phenantolyl group, 2-phenantolyl group, 3-phenantolyl group, 4-phenantolyl group, 9-phenantolyl group.

A heteroaryl group as described in this specification is typically a cyclic aromatic group consisting of four to ten carbon atoms and at least one heteroatom, each of which may independently be substituted. Examples of substituents are alkyl groups, or two alkyl groups which, together with the ring carbons to which they are bonded, form a further ring. Examples of heteroatoms in this context are an oxygen atom, nitrogen atom, phosphorus atom, boron atom, selenium atom or sulphur atom. Examples of a heteroaryl group are furyl group, thienyl group, pyrrolyl group or imidazolyl group.

An aryloxy group as described in this specification is typically an aryl group, where aryl has already been defined above, bonded covalently to an oxygen atom. Examples of an aryloxy group are phenyloxy or naphthyloxy.

An aralkyl group as described in this specification is typically an aryl group, where aryl has already been defined above, bonded covalently to an alkyl group. This group may, for example, be substituted by alkyl groups or halogen atoms. One example of an aralkyl group is benzyl.

The average molar mass ($M_n$) of the oligomeric or polymeric compound of this invention is in the range of 800 to 4 000 000 g/mol, preferably in the range from 2000 to 2 000 000 g/mol, more preferably in the range from 4000 to 400 000 g/mol. The average molar mass is determined by means of size exclusion chromatography (polystyrene standard). In general, the oligomeric or polymeric compound of the inventive general formula I of this invention consists of 2 and 5000 repeat units, preferably of 10 to 1000 repeat units.

The oligomeric or polymeric compounds of the inventive general formula I of this invention may be either homopolymers or copolymers. Homopolymers are polymers which have been synthesized only from one monomer. Copolymers are polymers which have been synthesized from two or more polymers. If two or more monomers are used in the synthesis, the monomers of the repeat units of the oligomeric or polymeric compound of this invention may be present in the oligomeric or polymeric compound in random distribution, as blocks or in alternation. The oligomeric or polymeric compounds of this invention may either be in linear or crosslinked form. Crosslinking can be effected, for example, via copolymerization with a small proportion of an organic molecule having two polymerizable groups, preferably a more highly functionalized monomer.

The oligomeric or polymeric compounds of the inventive general formula I are synthesized by the polymerization of a 9,10-bis(1,3-dithiol-2-ylidene)-9,10-dihydroanthracene compound of the general formula I'

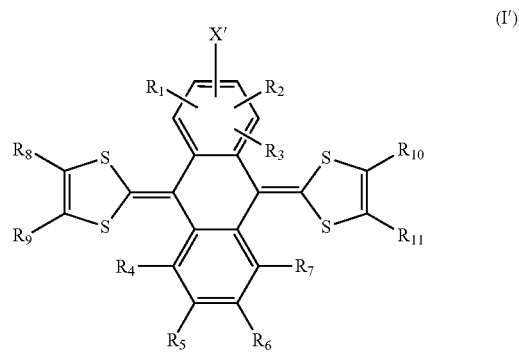

(I')

X' here is preferably an organic polymerizable group typically consisting of an organic double bond, or an organic triple bond, or an oxirane or an aziridine. Particular preference is given to organic polymerizable groups shown in the formulae II' to VIII'.

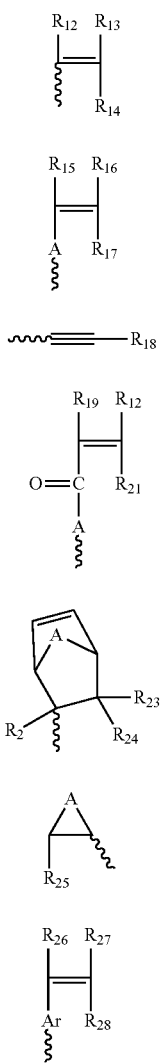
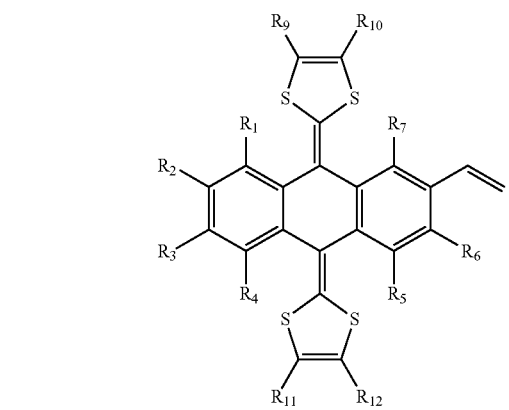
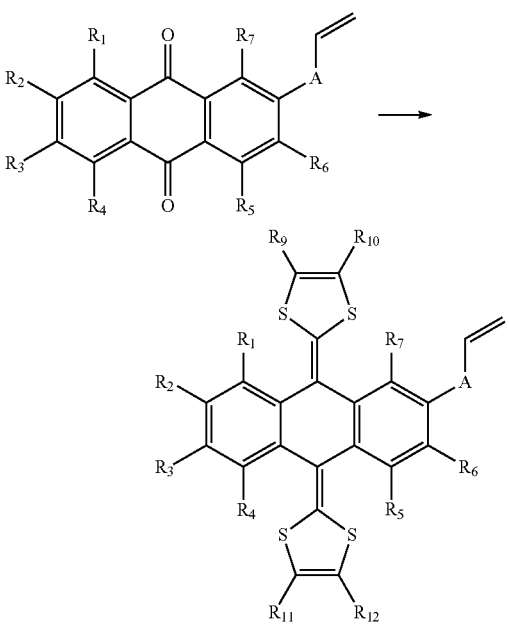
with the definitions already described above again for $R_{12}$ to $R_{28}$, A and Ar.
A 9,10-bis(1,3-dithiol-2-ylidene)-9,10-dihydroanthracene compound of the general formula I' can be prepared by the combination of known reactions.
The preparation of the compound of the general formula I' is shown in Schemes 1-7 below, but is not restricted thereto.
Scheme 1:
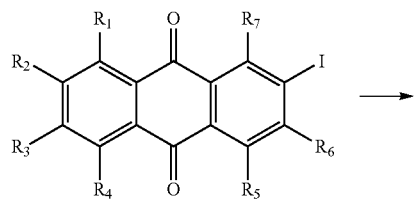

Scheme 3:
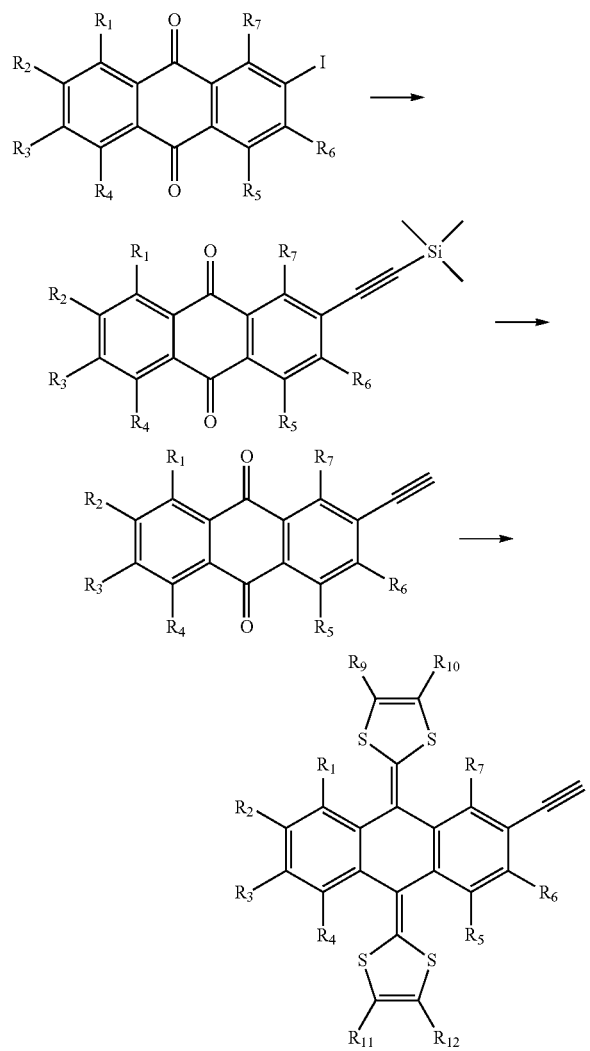
Scheme 4:
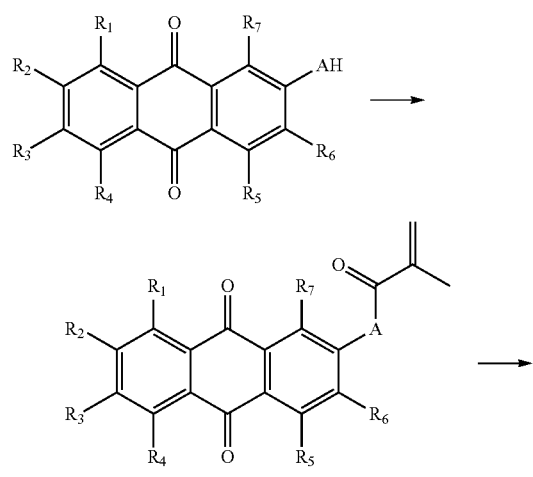
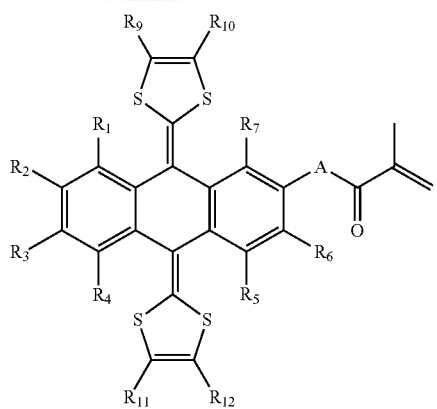
Scheme 5:
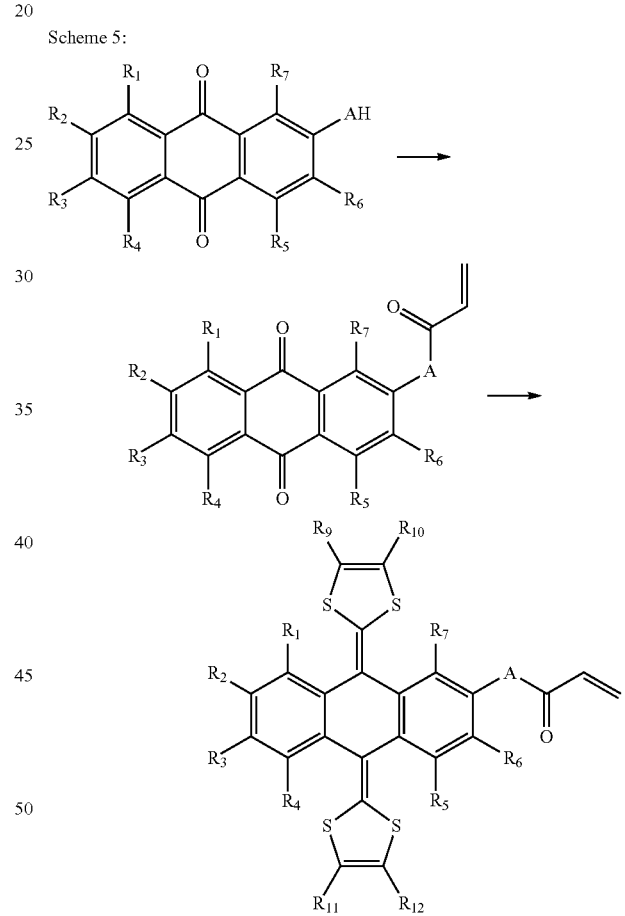
Scheme 6:
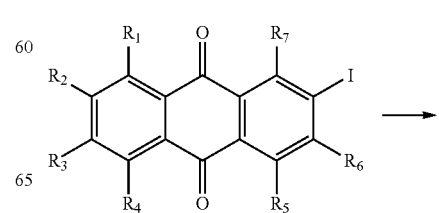

-continued

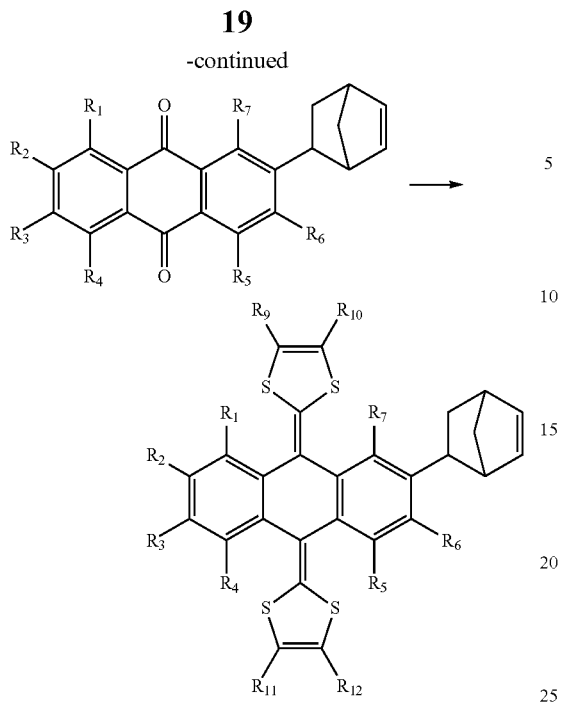

Scheme 7:

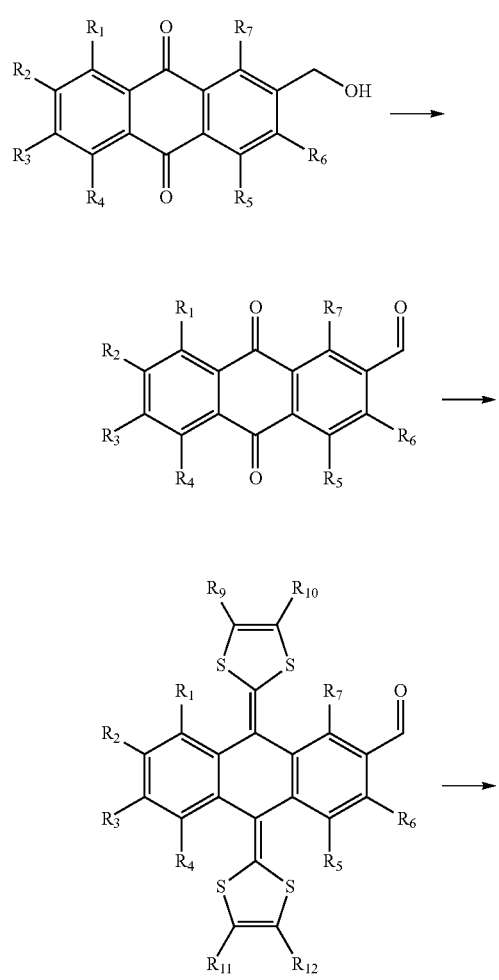

-continued

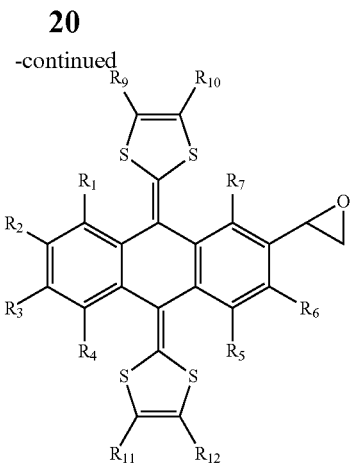

Methods known per se are sufficient for synthesis of the compound of the abovementioned general formula according to the above Schemes 1-7.

If X' in the general formula I' corresponds to the abovementioned formula the compound of the formula I' can be synthesized by a known method of polystyrene synthesis and derivatives thereof. Preferably, the abovementioned compound I' is synthesized by radical polymerization, for example free-radical polymerization, but also a controlled radical polymerization method, for example reversible addition-fragmentation chain transfer polymerization (RAFT), atom transfer radical polymerization (ATRP) or nitroxide-mediated polymerization (NMP), within a temperature range from −30 to 150° C., advantageously within a temperature range from 40 to 120° C., in a solvent and in a reaction time of 0.1 to 100 hours, using an initiator, for example azo compounds or peroxides, preferably benzoyl peroxide or 2,2'-azobisisobutyronitrile. There are barely any restrictions for solvents used. Preference is given to organic solvents, for example N,N'-dimethylformamide, N,N'-dimethylacetamide, dimethyl sulphoxide, N-methylpyrrolidone, dichloromethane, 1,2-dichloroethane, toluene, xylene, chlorobenzene or o-dichlorobenzene.

Likewise preferably, the abovementioned compound is synthesized by cationic polymerization within a temperature range from −30 to 150° C., advantageously within a temperature range from −20 to 50° C., in a solvent and a reaction time of 0.1 to 100 hours, using a catalyst, for example Lewis acids or protic acids, preferably sulphuric acid, nitric acid, perchloric acid, boron trifluoroetherate complex, aluminium trichloride, tin tetrachloride or titanium tetrachloride. There are barely any restrictions for solvents used. Preference is given to organic solvents, for example N,N'-dimethylformamide, N,N'-dimethylacetamide, dimethyl sulphoxide, N-methylpyrrolidone, dichloromethane, tetrahydrofuran, 1,4-dioxolane, 1,2-dichloroethane, toluene, xylene, chlorobenzene or o-dichlorobenzene.

Likewise preferably, the abovementioned compound is synthesized by anionic polymerization within a temperature range from −78 to 150° C., advantageously within a temperature range from −50 to 50° C., in a solvent and a reaction time of 0.1 to 100 hours, using a catalyst, for example Lewis bases or bases, preferably metal amides such as sodium amide and $LiC_2H_5$, alkoxides such as methoxide or ethoxide, hydroxides such as sodium hydroxide or potassium hydroxide, cyanides, phosphines, amines or organometallic compounds, for example n-butyllithium or vinylmagnesium bromide. There are barely any restrictions for solvents used. Preference is given to organic solvents, for example tetrahydrofuran, 1,4-dioxolane, diethyl ether, tert-butyl methyl ether, toluene, xylene, chlorobenzene or o-dichlorobenzene.

Likewise preferably, the abovementioned compound is synthesized by anionic group transfer polymerization within a temperature range from −30 to 150° C., advantageously within a temperature range from −20 to 50° C., in a solvent and a reaction time of 0.1 to 100 hours, using an initiator, for example a silyl ketene acetal, and using a catalyst, for example inorganic salts, preferably fluorides, azides or cyanides, or Lewis acids, preferably zinc chloride or dialkylaluminium chloride. There are barely any restrictions for solvents used. Preference is given to organic solvents, for example N,N'-dimethylformamide, N,N'-dimethylacetamide, dimethyl sulphoxide, N-methylpyrrolidone, dichloromethane, 1,2-dichloroethane, tetrahydrofuran, 1,4-dioxolane, diethyl ether, tort-butyl methyl ether, toluene, xylene, chlorobenzene or o-dichlorobenzene.

If X' in the general formula 1' corresponds to the abovementioned formula III', the compound of the formula I' can be synthesized by a known method of polyvinyl ether synthesis and derivatives thereof. Preferably, the abovementioned compound I' is synthesized by cationic polymerization within a temperature range from −30 to 150° C., advantageously within a temperature range from −20 to 50° C., in a solvent and a reaction time of 0.1 to 100 hours, using a catalyst, for example Lewis acids or erotic acids, preferably sulphuric acid, nitric acid, perchloric acid, boron trifluoroetherate complex, aluminium trichloride, tin tetrachloride or titanium tetrachloride.

There are barely any restrictions for solvents used. Preference is given to organic solvents, for example N,N'-dimethylformamide, N,N'-dimethylacetamide, dimethyl sulphoxide, N-methylpyrrolidone, dichloromethane, tetrahydrofuran, 1,4-dioxolane, 1,2-dichloroethane, toluene, xylene, chlorobenzene or o-dichlorobenzene.

If X' in the general formula I' corresponds to the abovementioned formula IV', the compound of the formula I' can be synthesized by a known method of polyacetylene synthesis and derivatives thereof. Preferably, the abovementioned compound I' is synthesized by metal-catalysed polymerization within a temperature range from −30 to 150° C., advantageously within a temperature range from 0 to 100° C., in a solvent and a reaction time of 0.1 to 100 hours, using a catalyst, for example a Wilkinson catalyst, a Ziegler-Matta catalyst, a Luttinger catalyst, a molybdenum complex, a tungsten complex, a rhodium complex, or an electrochemical polymerization method using nickel bromide. There are barely any restrictions for solvents used. Preference is given to organic solvents, for example N,N'-dimethylformamide, N,N'-dimethylacetamide, dimethyl sulphoxide, N-methylpyrrolidone, dichloromethane, 1,2-dichloroethane, toluene, xylene, chlorobenzene or o-dichlorobenzene.

If X' in the general formula corresponds to the abovementioned formula V', the compound of the formula I' can be synthesized by a known method of polyacrylate synthesis and derivatives thereof. Preferably, the abovementioned compound I' is synthesized by free-radical polymerization, but also controlled radical polymerization methods, for example reversible addition-fragmentation chain transfer polymerization (RAFT), atom transfer radical polymerization (ATRP), cobalt-mediated radical polymerization (CMRP) or nitroxide-mediated polymerization (NMP), within a temperature range from −30 to 150° C., advantageously within a temperature range from 40 to 120° C., in a solvent and in a reaction time of 0.1 to 100 hours, using an initiator, for example azo compounds or peroxides, preferably benzoyl peroxide or 2,2'-azobisisobutyronitrile.

There are barely any restrictions for solvents used. Preference is given to organic solvents, for example N,N'-dimethylformamide, N,N'-dimethylacetamide, dimethyl sulphoxide, N-methylpyrrolidone, dichloromethane, 1,2-dichloroethane, toluene, xylene, chlorobenzene or o-dichlorobenzene.

Likewise preferably, the abovementioned compound I' is synthesized by anionic polymerization within a temperature range from −78 to 150° C., advantageously within a temperature range from −50 to 50° C., in a solvent and a reaction time of 0.1 to 100 hours, using a catalyst, for example Lewis bases or bases, preferably metal amides such as sodium amide and $LiC_2H_5$, alkoxides such as methoxide or ethoxide, hydroxides such as sodium hydroxide or potassium hydroxide, cyanides, phosphines, amines or organometallic compounds, for example n-butyllithium or vinylmagnesium bromide. There are barely any restrictions for solvents used. Preference is given to organic solvents, for example tetrahydrofuran, 1,4-dioxolane, diethyl ether, tort-butyl methyl ether, toluene, xylene, chlorobenzene or o-dichlorobenzene.

Likewise preferably, the abovementioned compound I' is synthesized by anionic group transfer polymerization within a temperature range from −78 to 150° C., advantageously within a temperature range from −20 to 50° C., in a solvent and a reaction time of 0.1 to 100 hours, using an initiator, for example a silyl ketene acetal, and using a catalyst, for example inorganic salts, preferably fluorides, azides or cyanides, or Lewis acids, preferably zinc chloride or dialkylaluminium chloride. There are barely any restrictions for solvents used. Preference is given to organic solvents, for example N,N'-diniethylforinamide, N,N'-ditnethylacetamide, dimethyl sulphoxide, N-methylpyrrolidone, dichloromethane, 1,2-clichloroethane, tetrahydrofuran, 1,4-clioxolane, diethyl ether, tea-butyl methyl ether, toluene, xylene, chlorobenzene or o-dichlorobenzene.

If X' in the general formula I' corresponds to the abovementioned formula VII', the compound of the formula can be synthesized by a known method of polynorbornene synthesis and derivatives thereof. Preferably, the abovementioned compound is synthesized by metal-catalysed polymerization within a temperature range from −30 to 150° C., advantageously within a temperature range from 0 to 100° C., in a solvent and in a reaction time of 0.1 to 100 hours, using a catalyst, for example a Grubbs catalyst, a molybdenum complex, a tungsten complex or a ruthenium complex.

There are barely any restrictions for solvents used. Preference is given to organic solvents, for example N,N'-dimethylfotniamicle, N,N'-dimethylacetamide, dimethyl sulphoxide, N-methylpyrrolidone, dichloromethane, 1,2-dichloroethane, tetrahydrofuran, toluene, xylene, chlorobenzene or o-dichlorobenzene.

If X' in the general formula I' corresponds to the abovementioned formula VII', the compound of the formula I' can be synthesized by a known method of polyethylene glycol synthesis and derivatives thereof.

Preferably, the abovementioned compound P is synthesized by cationic polymerization within a temperature range from −30 to 150° C., advantageously within a temperature range from 40 to 120° C., in a solvent and a reaction time of 0.1 to 100 hours, using a catalyst, for example Lewis acids or erotic acids, preferably sulphuric acid, nitric acid, perchloric acid, boron trifluoroetherate complex, aluminium trichloride, tin tetrachloride, diethylzinclwater or titanium tetrachloride.

There are barely any restrictions for solvents used. Preference is given to organic solvents, for example N,N'-dimethylformamide, N,N'-dimethylacetamide, dimethyl sulphoxide, N-methylpyrrolidone, dichloromethane, tetrahydrofuran, 1,4-dioxolane, 1,2-dichloroethane, toluene, xylene, chlorobenzene or o-dichlorobenzene.

Likewise preferably, the abovementioned compound I' is synthesized by anionic polymerization within a temperature range from −78 to 150° C., advantageously within a temperature range from −50 to 50° C., in a solvent and a reaction time of 0.1 to 100 hours, using a catalyst, for example Lewis bases or bases, preferably metal amides such as sodium amide and $LiC_2H_5$, alkoxides such as methoxide or ethoxide, hydroxides such as sodium hydroxide or potassium hydroxide, cyanides, phosphines, amines or organometallic compounds, for example n-butyllithium or vinylmagnesium bromide. There are barely any restrictions for solvents used. Preference is given to organic solvents, for example tetrahydrofuran, 1,4-dioxalane, diethyl ether, tert-butyl methyl ether, toluene, xylene, chlorobenzene or o-dichlorobenzene.

If X' in the general formula I' corresponds to the abovementioned formula VIII', the compound of the formula I' can be synthesized by a known method of polystyrene synthesis and derivatives thereof. Preferably, the abovementioned compound I' is synthesized by radical polymerization, for example free-radical polymerization, but also a controlled radical polymerization method, for example reversible addition-fragmentation chain transfer polymerization (RAFT), atom transfer radical polymerization (ATRP) or nitroxide-mediated polymerization (NMP), within a temperature range from −30 to 150° C., advantageously within a temperature range from 40 to 120° C., in a solvent and in a reaction time of 0.1 to 100 hours, using an initiator, for example azo compounds or peroxides, preferably benzoyl peroxide or 2,2'-azobisisobutyronitrile. There are barely any restrictions for solvents used. Preference is given to organic solvents, for example N,N'-dimethlformamide, N,N'-dimethylacetamide, dimethyl sulphoxide, N-methylpyrrolidone, dichloromethane, 2-dichloroethane, toluene, xylene, chlorobenzene or o-dichlorobenzene.

Likewise preferably, the abovementioned compound I' is synthesized by cationic polymerization within a temperature range from −30 to 150° C., advantageously within a temperature range from −20 to 50° C., in a solvent and a reaction time of 0.1 to 100 hours, using a catalyst, for example Lewis acids or protic acids, preferably sulphuric acid, nitric acid, perchloric acid, boron trifluoroetherate complex, aluminium trichloride, tin tetrachloride or titanium tetrachloride. There are barely any restrictions for solvents used. Preference is given to organic solvents, for example N,N'-dimethylformamide, N,N'-dimethylacetamide, dimethyl sulphoxide, N-methylpyrrolidone, dichloromethane, tetrahydrofuran, 1,4-dioxolane, 1,2-dichloroethane, toluene, xylene, chlorobenzene or o-dichlorobenzene.

Likewise preferably, the abovementioned compound I' is synthesized by anionic polymerization within a temperature range from −78 to 150° C., advantageously within a temperature range from −50 to 50° C., in a solvent and a reaction time of 0.1 to 100 hours, using a catalyst, for example Lewis bases or bases, preferably metal amides such as sodium amide and $LiC_2H_5$, alkoxides such as methoxide or ethoxide, hydroxides such as sodium hydroxide or potassium hydroxide, cyanides, phosphines, amines or organometallic compounds, for example n-butyllithium or vinylmagnesium bromide. There are barely any restrictions for solvents used. Preference is given to organic solvents, for example tetrahydrofuran, 1,4-dioxalane, diethyl ether, tert-butyl methyl ether, toluene, xylene, chlorobenzene or o-dichlorobenzene.

Likewise preferably, the abovementioned compound I' is synthesized by anionic group transfer polymerization within a temperature range from −78 to 150° C., advantageously within a temperature range from −20 to 50° C., in a solvent and a reaction time of 0.1 to 100 hours, using an initiator, for example a silyl ketene acetal, and using a catalyst, for example inorganic salts, preferably fluorides, azides or cyanides, or Lewis acids, preferably zinc chloride or dialkyl-aluminium chloride. There are barely any restrictions for solvents used. Preference is given to organic solvents, for example N,N'-dimethylformamide, N,N'-dimethylacetamide, dimethyl sulphoxide, N-methylpyrrolidone, dichloromethane, 1,2-dichloroethane, tetrahydrofuran, 1,4-dioxolane, diethyl ether, tert-butyl methyl ether, toluene, xylene, chlorobenzene or o-dichlorobenzene.

In addition, the oligomeric or polymeric compounds of the inventive general formula I are synthesized by polymer-analogous reaction of a, 10-bis(1,3-dithiol-2-ylidene)-9,10-dihydroanthracene compound of the general formula I" with an oligomeric or polymeric compound of the general formula P'.

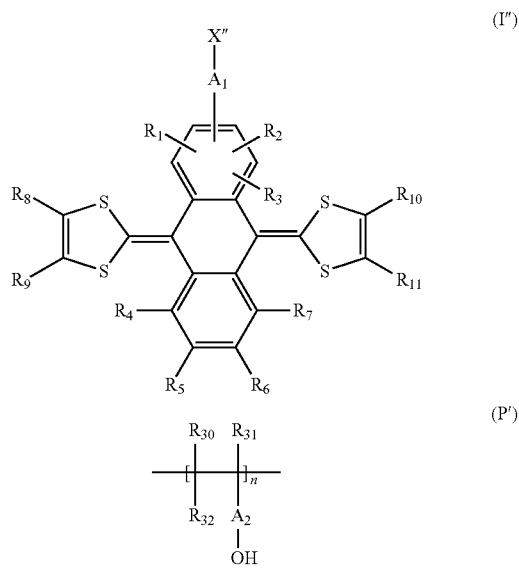

where
R$_1$ to R$_7$ and R$_{30}$ to R$_{32}$: may preferably each independently be hydrogen atoms, alkyl groups, alkenyl groups, alkynyl groups, alkoxy groups, alkylthio groups, haloalkyl groups, haloalkoxy groups, cycloalkyl groups, cycloalkoxy groups, aryl groups, heteroaryl groups, aryloxy groups, aralkyl groups, carboxylic acid groups, sulphonic acid groups, amino groups, monoalkylamino groups, dialkylamino groups, nitro groups, cyano groups, hydroxyl groups, alkylcarbonyl groups, alkenylcarbonyl groups, alkynylcarbonyl groups, carboxylic ester groups, carboxamide groups, sulphonic ester groups, thiol groups, halogen atoms or a combination of these groups or atoms, particular preference being given to hydrogen atoms as at least five of the R$_1$ to R$_7$ substituents and to non-hydrogen atoms, preferably halogen atoms, alkyl groups, alkoxy groups, cyano groups and/or nitro groups, as zero to two of the R$_1$ bis R$_7$ substituents, and/or to hydrogen atoms as at least two of the R$_{30}$ to R$_{32}$ substituents and to non-hydrogen atoms, preferably halogen atoms, alkyl groups, alkoxy groups, cyano groups and/or nitro groups, as zero to one of the R$_{30}$ to R$_{32}$ substituents, $R_8$ to $R_{11}$: may preferably each independently be hydrogen atoms, alkyl groups, alkenyl groups, alkynyl groups, alkoxy groups, alkylthio groups, haloalkyl groups, haloalkoxy groups, cycloalkyl groups, cycloalkoxy groups, aryl groups, heteroaryl groups, aryloxy groups, aralkyl groups, amino groups, monoalkylamino groups, dialkylamino groups, nitro groups, cyano groups, hydroxyl groups, alkylcarbonyl groups, alkenylcarbonyl groups, alkynylcarbonyl groups, carboxylic ester groups, carboxamide groups, sulphonic ester groups, thiol groups, halogen atoms or a combination of these groups or atoms, where the $R_8$ and $R_9$ substituents or the $R_{10}$ and $R_{11}$ substituents may form a further ring consisting of five to seven atoms (the ring may be aromatic, heteroaromatic or nonaromatic; if the ring is nonaromatic, it may consist of various groups, for example alkyl groups, alkenyl groups, alkynyl groups, alkoxy groups, alkylthio groups, haloalkyl groups, haloalkoxy groups, cycloalkyl groups, cycloalkoxy groups, aryl groups, heteroaryl groups, aryloxy groups, aralkyl groups, amino groups, monoalkylamino groups, dialkylamino groups, alkylcarbonyl groups, alkenylcarbonyl groups, alkynylcarbonyl groups, carboxylic ester groups, carboxamide groups, sulphonic ester groups; more preferably, $R_8$ to $R_{11}$ are the same and are each alkyl groups, such as typically methyl groups or ethyl groups, alkylthio groups, such as methylthio groups, or ethylthio groups and thiol groups), X'': is an electrophilic organic group which is attacked nucleophilically by the hydroxyl group of the compound P' and hence forms a covalent bond between the compound I'' and P' (preferably, X'' is an isocyanate group, a carbonyl halide group, where the halogen is preferably chlorine, bromine or iodine, a carboxylic acid group, a halogen atom, where the halogen is preferably chlorine, bromine or iodine, or a carbonyl group, an anhydride group), $A_1$ and $A_2$: are preferably a covalent bond, an alkyl group, an alkenyl group, an alkynyl group, an alkoxy group, an alkylthio group, a haloalkyl group, a haloalkoxy group, a cycloalkyl group, a cycloalkoxy group, an aryl group, a heteroaryl group, an aryloxy group, an aralkyl group, a monoalkylamino group, a dialkylamino group, an alkylcarbonyl group, an alkenylcarbonyl group, an alkynylcarbonyl group, a carboxylic ester group, a carboxamide group, a sulphonic ester group, where a covalent bond or an alkyl group as $A_1$ and $A_2$ is particularly advantageous, n: is an integer greater than or equal to 2.

The preparation of the compound of the inventive general formula I by polymer-analogous reaction from the abovementioned compounds I'' and P' and the preparation thereof is shown in Schemes 8-13 below, but is not restricted thereto.

Scheme 8:

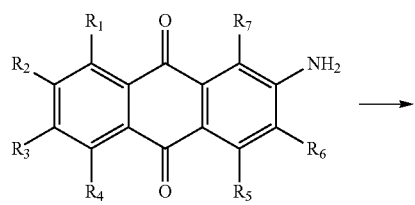

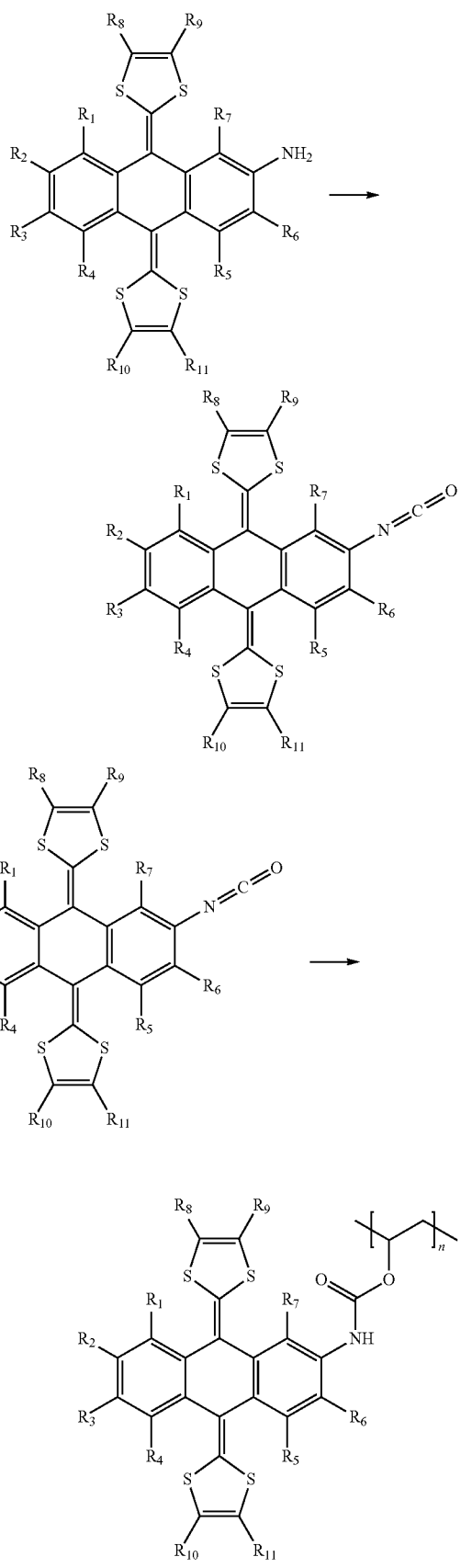

Scheme 9:
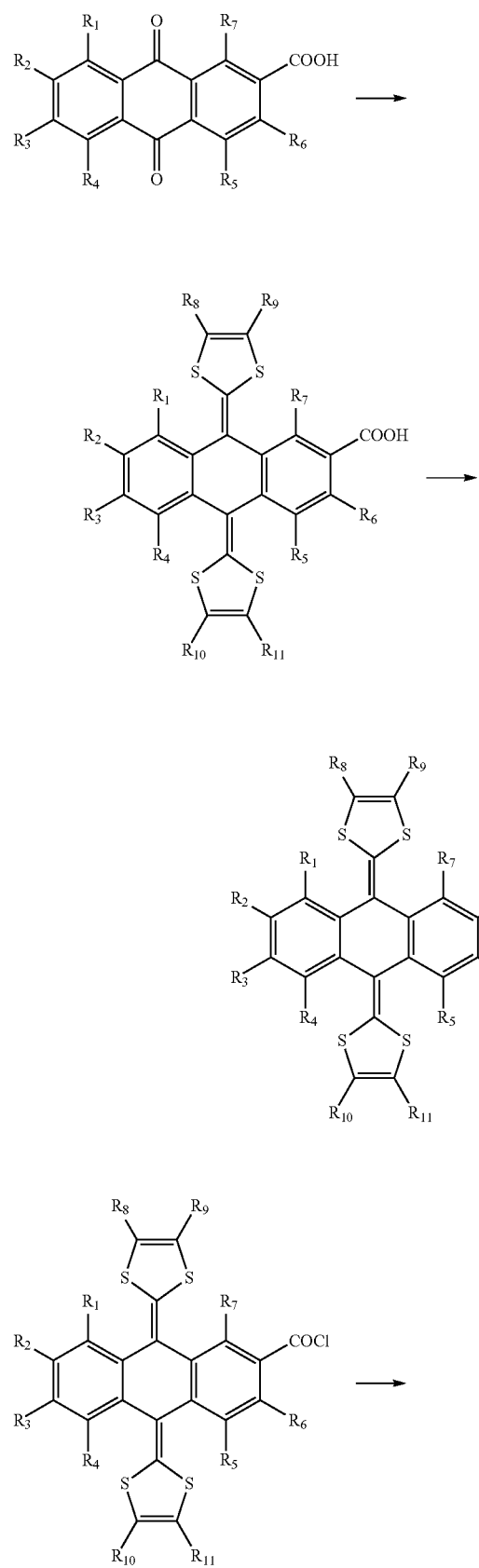
Scheme 10:
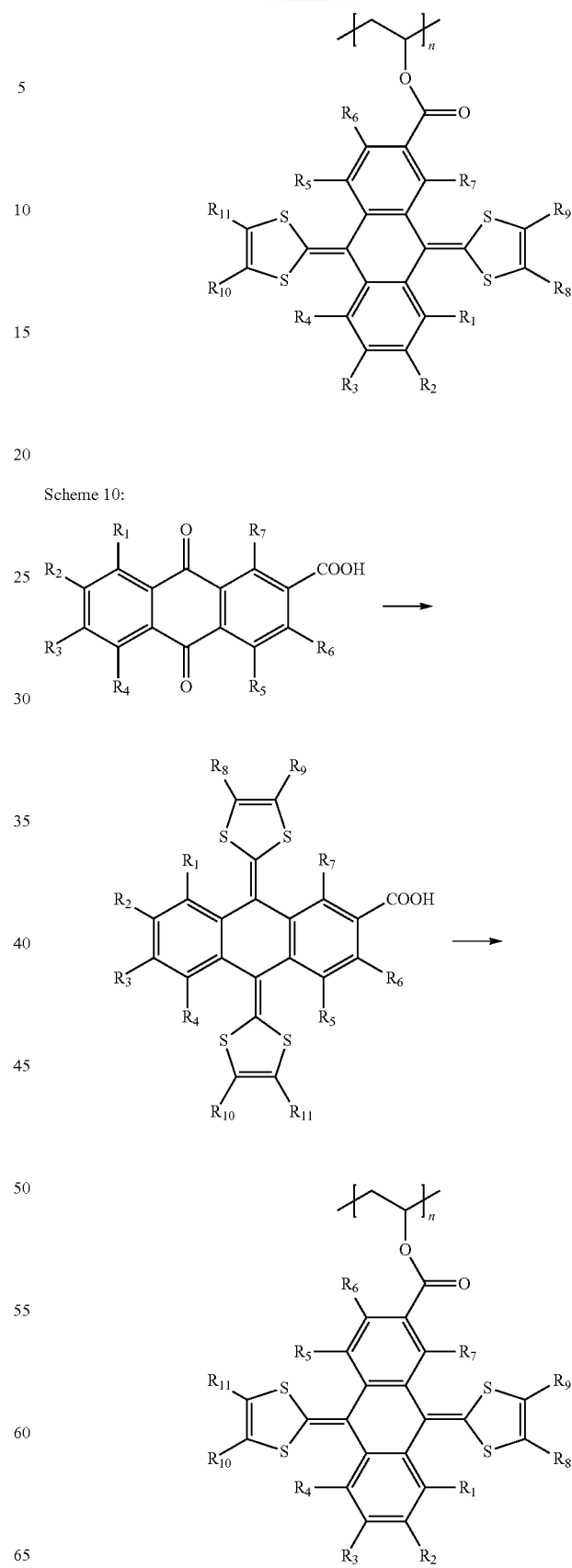

Scheme 11:
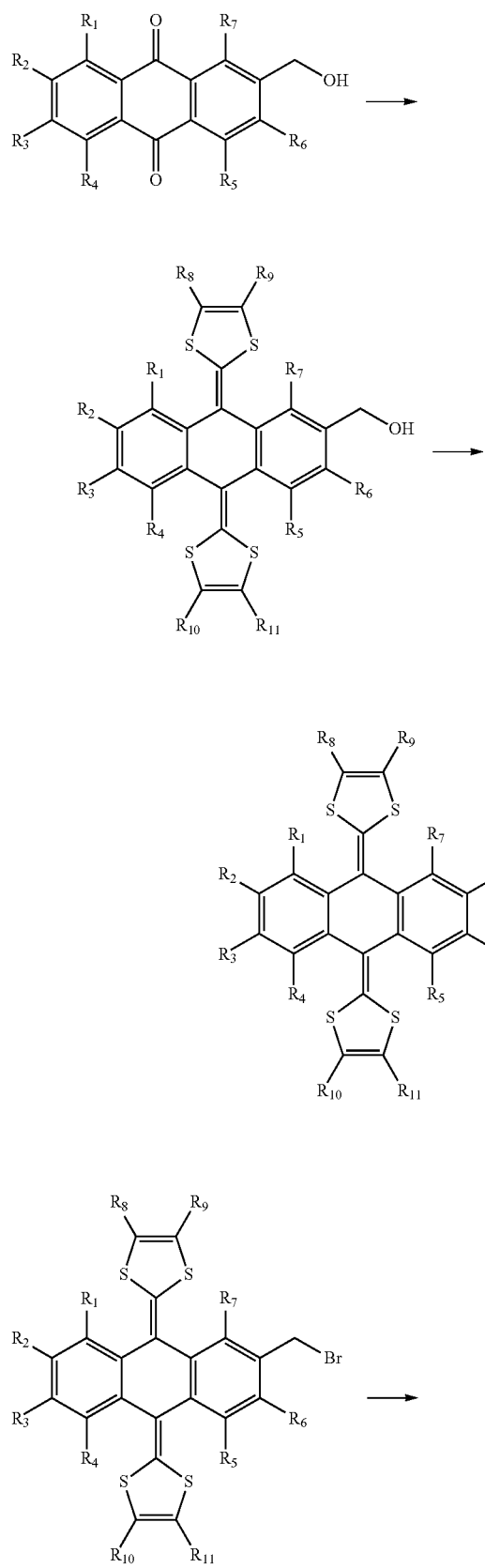
Scheme 12:
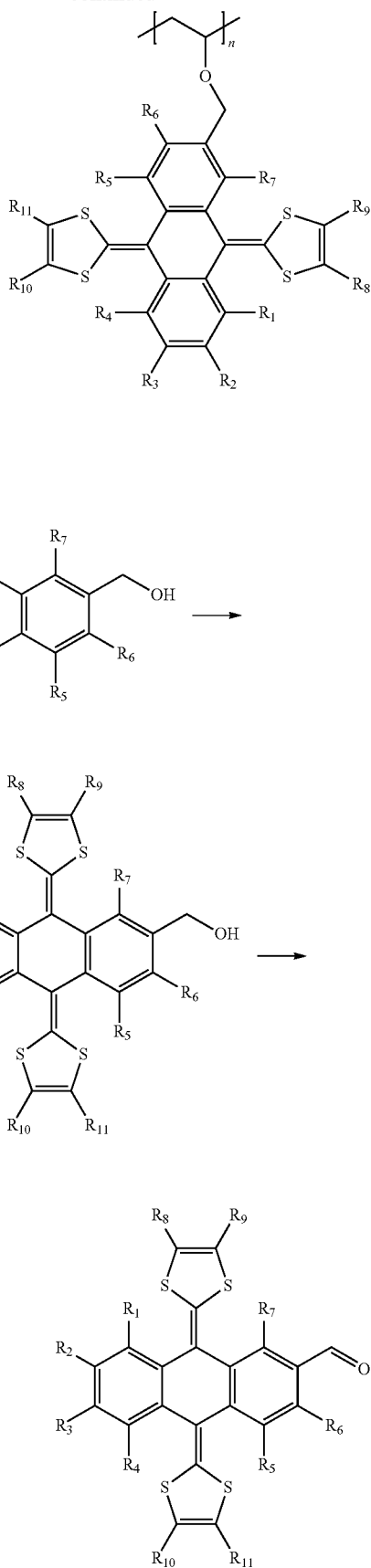

31
-continued
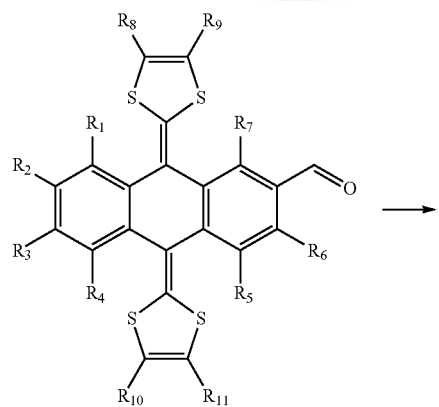
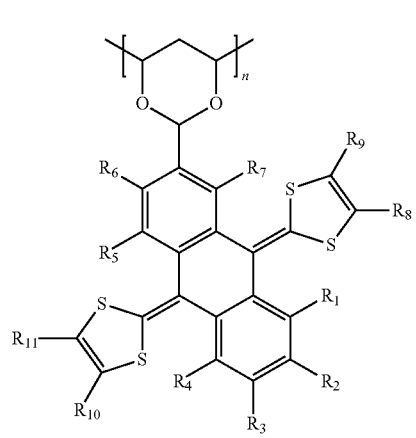
Scheme 13:
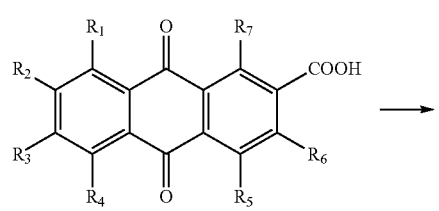
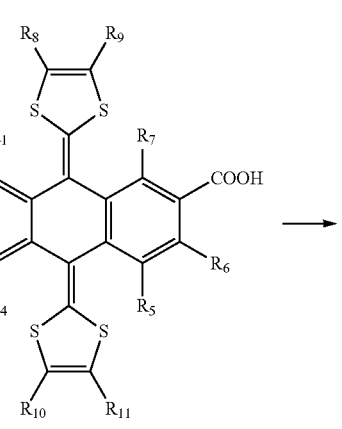
32
-continued
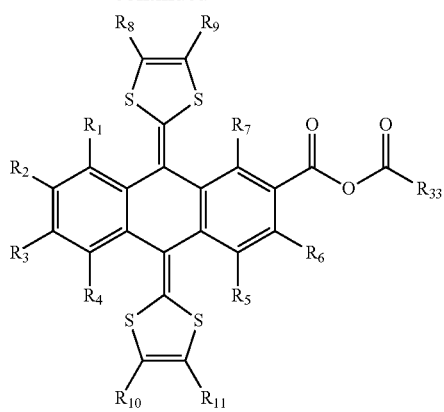
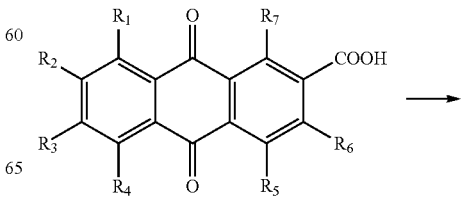
Scheme 13:
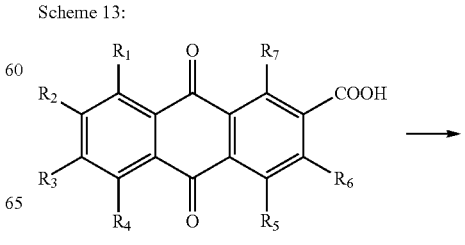

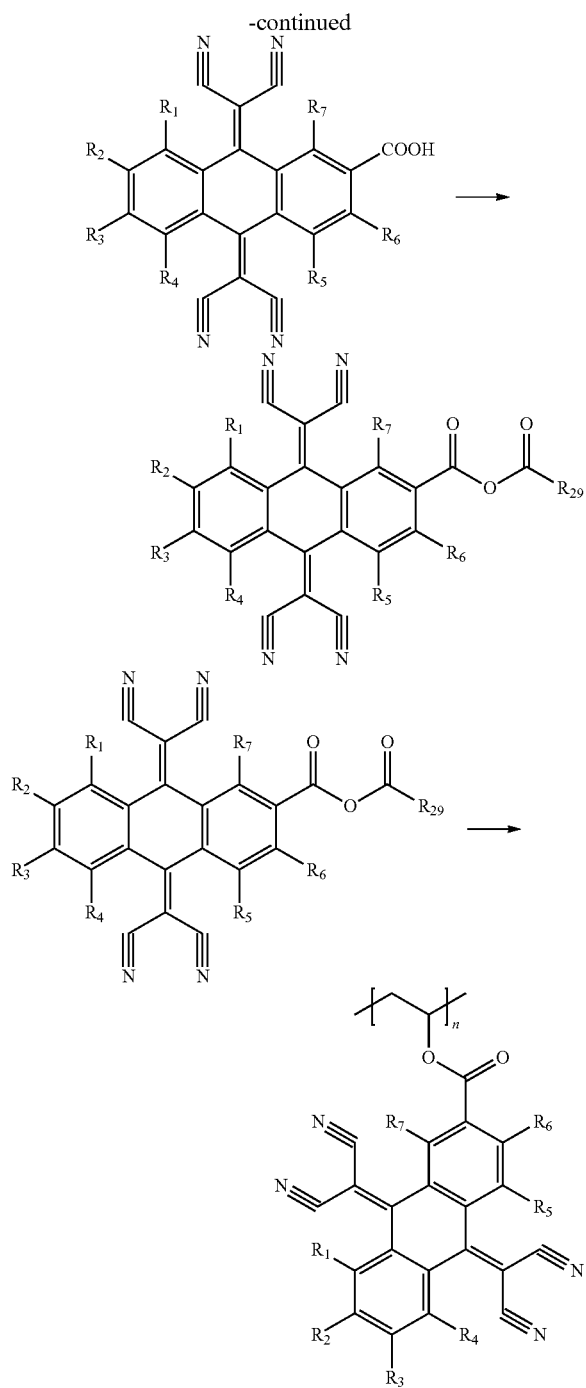

$R_{33}$ is preferably a hydrogen atom, an alkyl group, an alkenyl group, an alkynyl group, an alkoxy group, an alkylthio group, a cycloalkyl group, a cycloalkoxy group, an aryl group, a heteroaryl group, an aryloxy group, an aralkyl group. More preferably, $R_{33}$ is an alkyl group.

Methods known per se are sufficient for synthesis of the compound of the abovementioned inventive general formula I according to Schemes 8-13.

If X" in the general formula I" corresponds to an isocyanate group, the compound of the formula I can be synthesized by reaction of the compound I" with the compound P' by a known method of urethane synthesis and derivatives thereof. Preferably, the abovementioned compound I is synthesized within a temperature range from −78 to 150° C., advantageously within a temperature range from −40 to 120° C., in a solvent and in a reaction time of 0.1 to 100 hours. There are barely any restrictions for solvents used. Preference is given to aprotic organic solvents, for example N,N'-dimethylformamide, N,N'-dimethylacetamide, dimethyl sulphoxide, N-methylpyrrolidone, dichloromethane, 1,2-dichloroethane, toluene, xylene, chlorobenzene or o-dichlorobenzene.

If X" in the general formula I" corresponds to a carbonyl halide group, the compound of the formula I can be synthesized by reaction of the compound I" with the compound P' by a known method of carboxylic ester synthesis and derivatives thereof. Preferably, the abovementioned compound I is synthesized within a temperature range from −78 to 150° C., advantageously within a temperature range from −40 to 120° C., in a solvent and in a reaction time of 0.1 to 100 hours, using a catalyst, for example a pyridine derivative such as typically 4-(dimethylamino)pyridine, or a carbodinnide derivative such as typically N,N'-dicyclohexylcarbodiimide. There are barely any restrictions for solvents used. Preference is given to aprotic organic solvents, for example N,N'-dimethylformamide, N,N'-ditnethylacetamide, dimethyl sulphoxide, N-methylpyrrolidone, dichloromethane, 1,2-clichloroethane, toluene, xylene, chlorobenzene or o-dichlorobenzene.

If X" in the general formula I" corresponds to a carboxylic acid group, the compound of the formula I can be synthesized by reaction of the compound I" with the compound P' by a known method of carboxylic ester synthesis and derivatives thereof. Preferably, the abovementioned compound I is synthesized within a temperature range from −78 to 150° C., advantageously within a temperature range from −40 to 120° C., in a solvent and in a reaction time of 0.1 to 100 hours, using a catalyst, for example a pyridine derivative such as typically 4-(ditnethylamino)pyridine, or a carbodiimide derivative such as typically N,N'-dicyclohexylcarbodiimide. There are barely any restrictions for solvents used.

Preference is given to aprotic organic solvents, for example N,N'-dimethylformamide, N,N'-ditnethylacetamide, dimethyl sulphoxide, N-methylpyrrolidone, dichloromethane, 1,2-clichloroethane, toluene, xylene, chlorobenzene or o-dichlorobenzene.

If X" in the general formula I" corresponds to a halogen atom, the compound of the formula I can be synthesized by reaction of the compound I" with the compound P' by a known method of ether synthesis and derivatives thereof. Preferably, the abovementioned compound I is synthesized within a temperature range from −78 to 150° C., advantageously within a temperature range from −40 to 120° C., in a solvent and in a reaction time of 0.1 to 100 hours, using a catalyst, for example a base such as sodium hydride, sodium hydroxide, potassium tert-butoxide, DBU or DBN. There are barely any restrictions for solvents used. Preference is given to aprotic organic solvents, for example N,N'-dimethylformamide, N,N'-ditnethylacetarnide, dimethyl sulphoxide, N-methylpyrrolidone, dichloromethane, 1,2-clichloroethane, toluene, xylene, chlorobenzene or o-dichlorobenzene.

If X" in the general formula I" corresponds to a carbonyl group, the compound of the formula I can be synthesized by reaction of the compound I" with the compound P' by a known method of acetal synthesis and derivatives thereof. Preferably, the abovementioned compound I is synthesized within a temperature range from −78 to 150° C., advantageously within a temperature range from −40 to 120° C., in a solvent and in a reaction time of 0.1 to 100 hours, using a catalyst, for example protic acids such as p-toluenesulphonic acid, hydrochloric acid, sulphuric acid or trifluoroacetic acid. There are barely any restrictions for solvents used. Preference is given to aprotic organic solvents, for example N,N'-dimethylformamide, N,N'-dimethylacetarnide, dimethyl sulphoxide, N-methylpyrrolidone, dichloromethane, 1,2-dichloroethane, toluene, xylene, chlorobenzene or o-dichlorobenzene.

If X" in the general formula I" corresponds to an anhydride group, the compound of the formula I can be synthesized by reaction of the compound I" with the compound P' by a known method of carboxylic ester synthesis and derivatives thereof. Preferably, the abovementioned compound I is synthesized within a temperature range from −78 to 150° C., advantageously within a temperature range from −40 to 120° C., in a solvent and in a reaction time of 0.1 to 100 hours, using a catalyst, for example a pyridine derivative such as typically 4-(dimethylamino)pyridine, or a carbodiimide derivative such as typically N,N'-dicyclohexylcarbodiimide. There are barely any restrictions for solvents used. Preference is given to aprotic organic solvents, for example N,N'-dimethylformamide, N,N'-dimethylacetamide, dimethyl sulphoxide, N-methylpyrrolidone, dichloromethane, 1,2-dichloroethane, toluene, xylene, chlorobenzene or o-dichlorobenzene.

In addition, the oligomeric or polymeric compounds of the inventive general formula I are synthesized by polymer-analogous reaction of a 9,10-bis(1,3-dithiol-2-ylidene)-9,10-dihydroanthracene compound of the general formula I'" with an oligomeric or polymeric compound of the general formula P'".

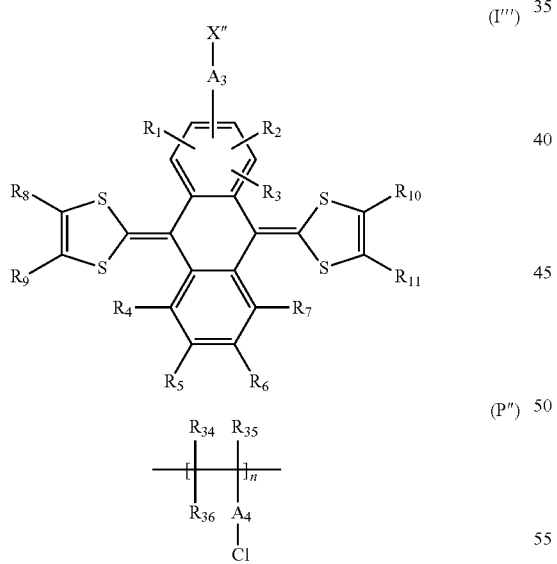

where
$R_1$ to $R_7$: may preferably each independently be hydrogen atoms, alkyl groups, alkenyl groups, alkynyl groups, aikoxy groups, alkylthio groups, haloalkyl groups, haloalkoxy groups, cycloalkyl groups, cycloalkoxy groups, aryl groups, heteroaryl groups, aryloxy groups, aralkyl groups, carboxylic acid groups, sulphonic acid groups, amino groups, monoalkylamino groups, dialkylamino groups, nitro groups, cyano groups, alkylcarbonyl groups, alkenylcarbonyl groups, alkynylcarbonyl groups, carboxylic ester groups, carboxamide groups, sulphonic ester groups, halogen atoms or a combination of these groups or atoms, particular preference being given to hydrogen atoms as at least five of the $R_1$ to $R_7$ substituents and to non-hydrogen atoms, preferably halogen atoms, alkyl groups, alkoxy groups, cyano groups and/or nitro groups, as zero to two of the $R_1$ bis $R_7$ substituents and/or hydrogen atoms, $R_8$ to $R_{11}$: may preferably each independently be hydrogen atoms, alkyl groups, alkenyl groups, alkynyl groups, alkoxy groups, alkylthio groups, haloalkyl groups, haloalkoxy groups, cycloalkyl groups, cycloalkoxy groups, aryl groups, heteroaryl groups, aryloxy groups, aralkyl groups, amino groups, monoalkylamino groups, dialkylamino groups, nitro groups, cyano groups, hydroxyl groups, alkylcarbonyl groups, alkenylcarbonyl groups, alkynylcarbonyl groups, carboxylic ester groups, carboxamide groups, sulphonic ester groups, thiol groups, halogen atoms or a combination of these groups or atoms, where the $R_8$ and $R_9$ substituents or the $R_{10}$ and $R_{11}$ substituents may form a further ring consisting of five to seven atoms (the ring may be aromatic, heteroaromatic or nonaromatic; if the ring is nonaromatic, it may consist of various groups, for example alkyl groups, alkenyl groups, alkynyl groups, alkoxy groups, alkylthio groups, haloalkyl groups, haloalkoxy groups, cycloalkyl groups, cycloalkoxy groups, aryl groups, heteroaryl groups, aryloxy groups, aralkyl groups, amino groups, monoalkylamino groups, dialkylamino groups, alkylcarbonyl groups, alkenylcarbonyl groups, alkynylcarbonyl groups, carboxylic ester groups, carboxamide groups, sulphonic ester groups; more preferably, $R_8$ to $R_{11}$ are the same and are each alkyl groups, such as typically methyl groups or ethyl groups, alkylthio groups, such as methylthio groups, or ethylthio groups and thiol groups), $R_{34}$ to $R_{36}$: may preferably each independently be hydrogen atoms, alkyl groups, alkenyl groups, alkynyl groups, alkoxy groups, alkylthio groups, haloalkyl groups, haloalkoxy groups, cycloalkyl groups, cycloalkoxy groups, aryl groups, heteroaryl groups, aryloxy groups, aralkyl groups, carboxylic acid groups, sulphonic acid groups, amino groups, monoalkylamino groups, dialkylamino groups, nitro groups, cyano groups, alkylcarbonyl groups, alkenylcarbonyl groups, alkynylcarbonyl groups, carboxylic ester groups, carboxamide groups, sulphonic ester groups, halogen atoms or a combination of these groups or atoms. Most preferably, at least two of the $R_{34}$ to $R_{36}$ substituents are hydrogen atoms and 0 to 1 of the $R_{34}$ to $R_{36}$ substituents are non-hydrogen atoms, preferably halogen atoms, alkyl groups, alkoxy groups, cyano groups and/or nitro groups.

X'": is a nucleophilic organic group which nucleophilically attacks the atom adjacent to the halogen atom of the compound P'" and hence forms a covalent bond between the compound I'" and P'", preference being given to a hydroxyl group or a thiol group as X'", $A_3$ and $A_4$: are preferably a covalent bond, an alkyl group, an alkenyl group, an alkynyl group, an alkoxy group, an alkylthio group, a cycloalkyl group, a cycloalkoxy group, an aryl group, a heteroaryl group, an aryloxy group, an aralkyl group, a dialkylamino group, an alkylcarbonyl group, an alkenylcarbonyl group, an alkynylcarbonyl group, a carboxylic ester group, a carboxamide group, a sulphonic ester group, particular preference being given to a covalent bond or an alkyl group as $A_1$ and $A_2$, n: is an integer greater than or equal to 2.

The preparation of the compound of the general formula I with the aid of a polymer-analogous reaction from the abovementioned compounds I''' and P'' is shown in Schemes 14-15 below, but is not restricted thereto.

Scheme 14:

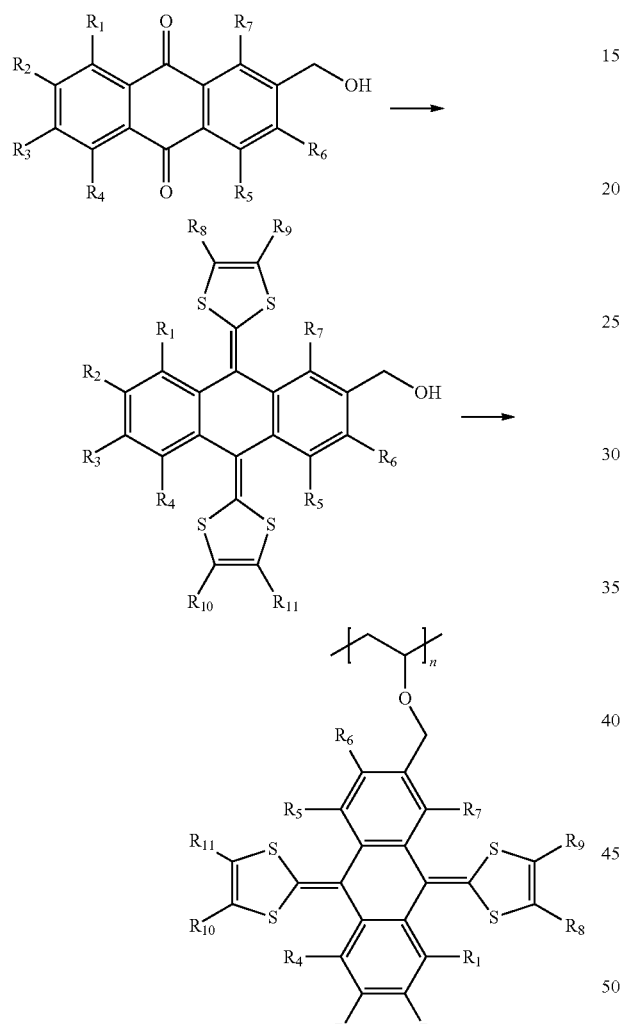

Scheme 15:

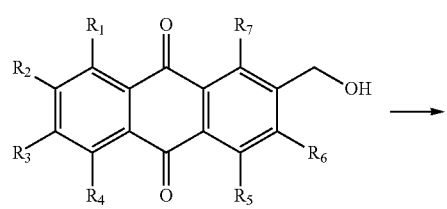

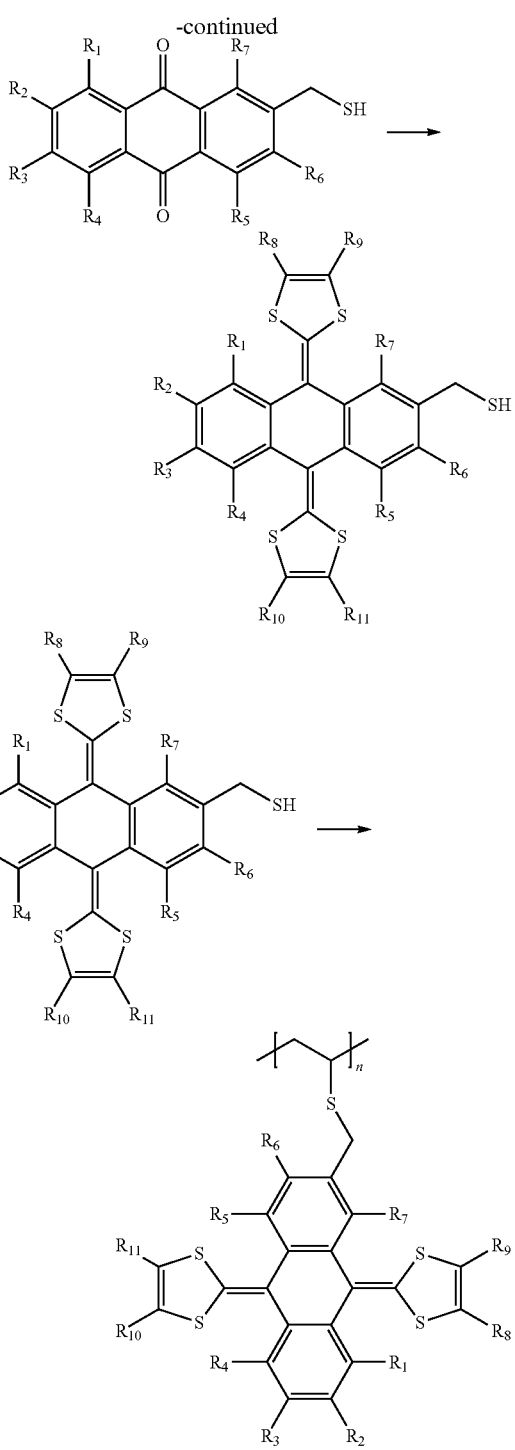

If X'' in the general formula I''' corresponds to a hydroxyl group or a thiol group, the compound of the formula I can be synthesized by reaction of the compound I''' with the compound P'' by a known method of ether synthesis and derivatives thereof. Preferably, the abovementioned compound I is synthesized within a temperature range from −78 to 150° C., advantageously within a temperature range from −40 to 120° C., in a solvent and in a reaction time of 0.1 to 100 hours, using a catalyst, for example a base such as sodium hydride, sodium hydroxide, potassium tert-butoxide, DBU or DBN. There are barely any restrictions for solvents used. Preference is given to aprotic organic solvents, for example N,N'-dimethylformamide, N,N'-dimethylacetamide, dimethyl sulphoxide, N-methylpyrrolidone, dichloromethane, 1,2-dichloroethane, toluene, xylene, chlorobenzene or o-dichlorobenzene.

In addition, the oligomeric or polymeric compounds of the inventive general formula I are synthesized by polymer-analogous reaction of a 9,10-bis(1,3-dithiol-2-ylidene)-9,10-dihydroanthracene compound of the general formula I'''' with an oligomeric or polymeric compound of the general formula P'''.

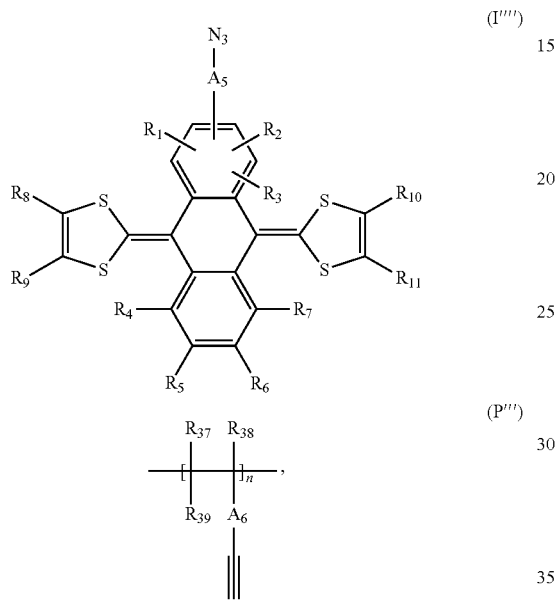

where
- $R_1$ to $R_7$: may preferably each independently be hydrogen atoms, alkyl groups, alkenyl groups, alkoxy groups, alkylthio groups, haloalkyl groups, haloalkoxy groups, cycloalkyl groups, cycloalkoxy groups, aryl groups, heteroaryl groups, aryloxy groups, aralkyl groups, carboxylic acid groups, sulphonic acid groups, amino groups, monoalkylamino groups, dialkylamino groups, nitro groups, cyano groups, hydroxyl groups, alkylcarbonyl groups, alkenylcarbonyl groups, alkynylcarbonyl groups, carboxylic ester groups, carboxamide groups, sulphonic ester groups, thiol groups, halogen atoms or a combination of these groups or atoms, particular preference being given to hydrogen atoms as at least five of the $R_1$ to $R_7$ substituents and to non-hydrogen atoms, preferably halogen atoms, alkyl groups, alkoxy groups, cyano groups and/or nitro groups, as zero to two of the $R_1$ bis $R_7$ substituents,
- $R_8$ to $R_{11}$: may preferably each independently be hydrogen atoms, alkyl groups, alkenyl groups, alkynyl groups, alkoxy groups, alkylthio groups, haloalkyl groups, haloalkoxy groups, cycloalkyl groups, cycloalkoxy groups, aryl groups, heteroaryl groups, aryloxy groups, aralkyl groups, amino groups, monoalkylamino groups, dialkylamino groups, nitro groups, cyano groups, hydroxyl groups, alkylcarbonyl groups, alkenylcarbonyl groups, alkynylcarbonyl groups, carboxylic ester groups, carboxamide groups, sulphonic ester groups, thiol groups, halogen atoms or a combination of these groups or atoms, where the $R_8$ and $R_9$ substituents or the $R_{10}$ and $R_{11}$ substituents may form a further ring consisting of five to seven atoms (the ring may be aromatic, heteroaromatic or nonaromatic; if the ring is nonaromatic, it may consist of various groups, for example alkyl groups, alkenyl groups, alkynyl groups, alkoxy groups, alkylthio groups, haloalkyl groups, haloalkoxy groups, cycloalkyl groups, cycloalkoxy groups, aryl groups, heteroaryl groups, aryloxy groups, aralkyl groups, amino groups, monoalkylamino groups, dialkylamino groups, alkylcarbonyl groups, alkenylcarbonyl groups, alkynylcarbonyl groups, carboxylic ester groups, carboxamide groups, sulphonic ester groups; more preferably, $R_8$ to $R_{11}$ are the same and are each alkyl groups, such as typically methyl groups or ethyl groups, alkylthio groups, such as methylthio groups, or ethylthio groups and thiol groups),
- $R_{37}$ to $R_{39}$: may preferably each independently be hydrogen atoms, alkyl groups, alkenyl groups, alkoxy groups, alkylthio groups, haloalkyl groups, haloalkoxy groups, cycloalkyl groups, cycloalkoxy groups, aryl groups, heteroaryl groups, aryloxy groups, aralkyl groups, carboxylic acid groups, sulphonic acid groups, amino groups, monoalkylamino groups, dialkylamino groups, nitro groups, cyano groups, hydroxyl groups, alkylcarbonyl groups, alkenylcarbonyl groups, alkynylcarbonyl groups, carboxylic ester groups, carboxamide groups, sulphonic ester groups, thiol groups, halogen atoms or a combination of these groups or atoms. Most preferably, at least two of the $R_{34}$ to $R_{36}$ substituents are hydrogen atoms and 0 to 1 of the $R_{34}$ to $R_{36}$ substituents are non-hydrogen atoms, preferably halogen atoms, alkyl groups, alkoxy groups, cyano groups and/or nitro groups.
- $A_5$ and $A_6$: are preferably a covalent bond, an alkyl group, an alkenyl group, an alkoxy group, an alkylthio group, a haloalkyl group, a haloalkoxy group, a cycloalkyl group, a cycloalkoxy group, an aryl group, a heteroaryl group, an aryloxy group, an aralkyl group, a monoalkylamino group, a dialkylamino group, an alkylcarbonyl group, an alkenylcarbonyl group, an alkynylcarbonyl group, a carboxylic ester group, a carboxamide group, a sulphonic ester group, particular preference being given to a covalent bond, an aryl group or an alkyl group as $A_5$ and $A_6$,
- n: is an integer greater than or equal to 2.

The preparation of the compound of the general formula I with the aid of a polymer-analogous reaction from the abovementioned compounds I''' and P''' is shown in Scheme 16 below, but is not restricted thereto.

Scheme 16:

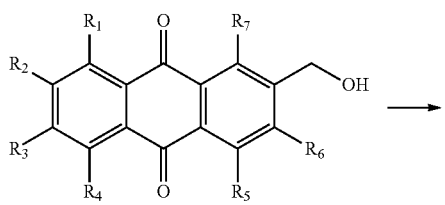

-continued

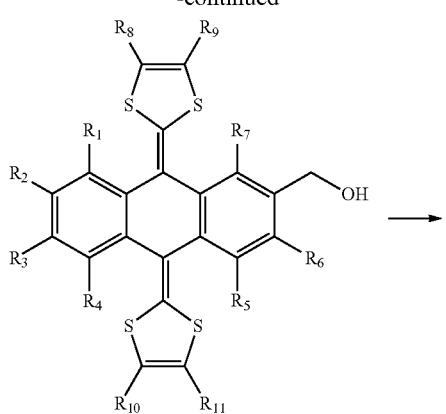

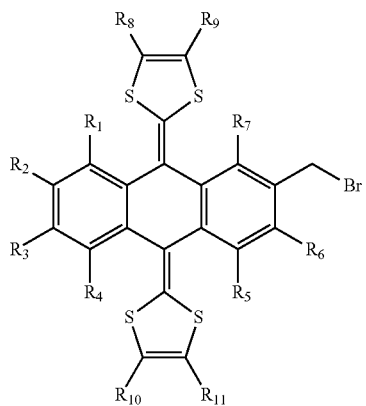

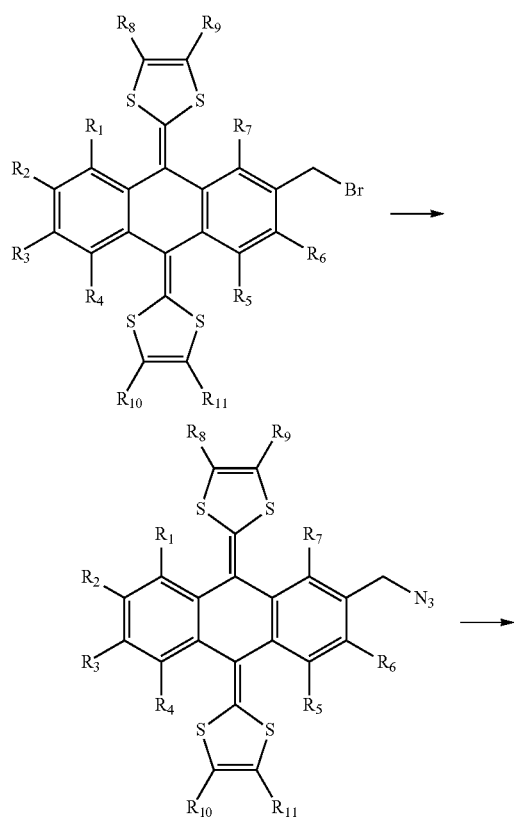

-continued

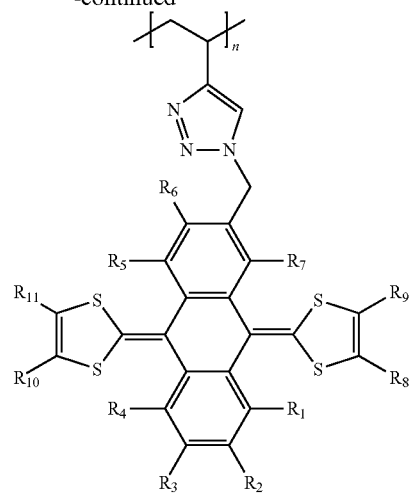

The compound of the formula I can also be synthesized by reaction of be compound I''' with the compound P''' by a known method of the azide/alkyne click reaction and derivatives thereof. Preferably, the abovementioned compound I is synthesized within a temperature range from −78 to 150° C., advantageously within a temperature range from −40 to 120° C., in a solvent and in a reaction time of 0.1 to 100 hours. There are barely any restrictions for solvents used. Preference is given to aprotic organic solvents, for example N,N'-dimethylformamide, N,N'-dimethylacetamide, dimethyl sulphoxide, N-methylpyrrolidone, dichloromethane, 1,2-dichloroethane, toluene, xylene, chlorobenzene or o-dichlorobenzene.

The oligomeric or polymeric compounds of this invention can appropriately be used as redox-active material for storage of electrical energy in an electrical charge storage means. A redox-active material for storage of electrical energy is a material which can store electrical charge and release it again, for example by accepting and releasing electrons. This material can be used, for example, as an active electrode material in an electrical charge storage means. Such electrical charge storage means for storage of electrical energy are, for example, secondary batteries (accumulators), redox flow batteries and supercapacitors.

A secondary battery consists of a negative electrode and a positive electrode which are separated from one another by a separator, and an electrolyte which surrounds the electrodes and these parator.

The separator is a porous layer which permits balancing of charge by being ion-permeable. The electrolyte is either a solvent with a salt dissolved the rein or an oligomeric or polymeric ion-conducting compound. The main object of the electrolyte is ion conductivity, which is needed to balance the charge.

An electrode may consist of a thin layer on a substrate, composed of a composite containing at least one conductivity additive, at least one binder additive and a redox-active material for charge storage, which may be the oligomeric or polymeric compound of the inventive general formula I. This composite is applied to a substrate with the aid of an electrode slurry.

Said layer on the substrate is formed, for example, by using a known method of film formation and derivatives thereof, preferably by various printing processes such as offset printing, screen printing, inkjet printing, or else by a dip-coating method, or a spin-coating method, in which case the layer including the oligomeric or polymeric compound of the inventive general formula I is processed with the aid of an electrode slurry. In this case, the oligomeric or polymeric compound of the invention, the conductivity additive and the binder additive may be suspended or dissolved in a solvent. The thickness of the abovementioned layer containing the oligomeric or polymeric compound of this invention is unlimited, but is preferably between 0.001 and 5000 μm, more preferably between 0.01 and 1000 μm.

The substrates used for the abovementioned electrodes are layers of conductive materials, preferably metals, such as platinum, gold, iron, copper, aluminium, lithium or a combination of these metals, and carbon materials, for example glassy carbon, graphite foil, graphene or carbon sheets, and oxide substances, for example indium tin oxide (ITO), indium zinc oxide (IZO), antimony zinc oxide (AZO), fluorine tin oxide (FTO) or antimony tin oxide (ATO).

Conductivity additives used for the layer are independently one or more electrically conductive materials, preferably carbon materials, for example carbon fibres, carbon nanotubes, graphite, carbon black or graphene, and electrically conductive polymers, for example polyanilines, polythiophenes, polyacetylenes, PEDOT:PSS or polyacenes. Particular preference is given to using carbon fibres.

Binder additives used for the substrate may independently be one or more materials having binder properties, preferably polymers, for example polytetrafluoroethylene, polyvinylidene fluoride, polyhexafluoropropylene, polyvinyl chloride, polycarbonate, polystyrene, polyacrylates, polymethacrylates, polysulphones, cellulose derivatives, and polyurethanes.

The electrode slurry is a solution or suspension consisting of any desired proportions of a redox-active material for storage of electrical energy, for example the oligomeric or polymeric compound of this invention as per formula I, a conductivity additive and a binder additive. Preferably, proportions of 5 to 100 percent by weight of a redox-active material for storage of electrical energy, 0 to 80 percent by weight of a conductivity additive and 0 to 10 percent by weight of a binder additive are used. Solvents used for the electrode slurry are independently one or more solvents, preferably solvents having a high boiling point, for example N-methyl-2-pyrrolidone, water, dimethyl sulphoxide, ethylene carbonate, propylene carbonate, dimethyl carbonate, methyl ethyl carbonate, gamma-butyrolactone, tetrahydrofuran, dioxolane, sulpholane, N,N'-dimethylformamide or N,N'-dimethylacetamide. The concentration of the redox-active material for storage of electrical energy in the abovementioned electrode slurry is preferably between 0.1 and 10 mg/ml, more preferably between 0.5 and 5 mg/ml.

The oligomeric or polymeric compounds of this invention as per general formula I may, according to the counterelectrode used, be used as active material for electrical charge storage either for the negative electrode or for the positive electrode.

If the oligomeric or polymeric compound of this invention as per formula I is used as redox-active material for electrical charge storage in the positive electrode, the redox-active material used for electrical charge storage in the negative electrode is an active material which exhibits a redox reaction at a lower electrochemical potential than the oligomeric or polymeric compound of this invention as per formula I. Preference is given here to using carbon materials, for example graphite, graphene, carbon black, carbon fibres or carbon nanotubes, and also metals or alloys, for example lithium, sodium, magnesium, lithium-aluminium, Li—Si, Li—Sn, Li—Ti, Si, SiO, $SiO_2$, Si—$SiO_2$ complex, Zn, Sn, SnO, $SnO_2$, PbO, $PbO_2$, GeO, $GeO_2$, $WO_2$, $MoO_2$, $Fe_2O_3$, $Nb_2O_5$, $TiO_2$, $Li_4Ti_5O_{12}$, and $Li_2Ti_3O_7$.

If the oligomeric or polymeric compound of this invention as per formula I is used as redox-active material for electrical charge storage in the negative electrode, the redox-active material used for electrical charge storage in the positive electrode is an active material which exhibits a redox reaction at a higher electrochemical potential than the oligomeric or polymeric compound of this invention as per formula I. Preference is given here to using organic redox-active material for electrical charge storage, for example an oligomeric or polymeric compound having a stable organic radical, an oligomeric or polymeric compound having an organosulphur unit, an oligomeric or polymeric compound having a quinone structure, an oligomeric or polymeric compound having a dione system, an oligomeric or polymeric compound having a disulphide bond and an oligomeric or polymeric compound having a phenanthrene structure and derivatives thereof or redox-active inorganic material for charge storage, for example $LiCO_2$, $LiMn_2O_4$, $LiNiO_2$, $LiNi_{0.5}Mn_{0.5}O_2$, $LiFePO_4$, $LiMnO_4$, $LiCoPO_4$, or $LiMnSiO_4$. If an abovementioned redox-active oligomeric or polymeric compound is used in the positive electrode, this compound may also be a composite consisting of this oligomeric or polymeric compound, a conductivity additive and a binder additive in any ratio. This composite may, as described above, be present as a layer on a substrate through a known film-forming process with the aid of an electrode slurry.

The redox-active material used for charge storage may also be air/oxygen. In this case, the positive electrode may consist of a conductivity additive, a binder additive and a redox catalyst. Preferably, redox catalysts used are an inorganic redox-active material, for example manganese oxide, or a redox-active organic material, for example an organic radical.

The abovementioned separator used in said secondary battery is a porous material, preferably membrane consisting of a polymeric compound, for example polyolefin, polyimide or polyester. The task of these parator is to separate the positive electrode from the negative electrode and to enable balancing of charge through permutation of ions.

The abovementioned electrolyte of said battery may be either a liquid or an oligomeric or polymeric compound having high ion conductivity.

If the electrolyte is liquid, it is independently composed of one or more solvents and one or more conductive salts.

The solvent of the electrolytes preferably consists independently of one or more solvents having a high boiling point and high ion conductivity but low viscosity, for example acetonitrile, dimethyl sulphoxide, ethylene carbonate, propylene carbonate, dimethyl carbonate, diethyl carbonate, methyl ethyl carbonate, gamma-butyrolactone, tetrahydrofuran, dioxolane, 1,2-dimethoxymethane, 1,2-dimethoxyethane, diglyme, triglyme, tetraglyme, ethyl acetate, 1,3-dioxolane or water.

The conductive salt in the electrolyte consists of a cation of the formula $M^{e+}$ and an anion of the formula $An^{f-}$ of the formula $(M^+)_a(An^{f-})_b$ where e and f are integers depending on the charge of M and An; a and b are integers which represent the molecular composition of the conductive salt.

Cations used in the abovementioned conductive salt are positively charged ions, preferably metals of the first and second main groups, for example lithium, sodium, potassium or magnesium, but also other metals of the transition groups, such as zinc, and organic cations, for example quaternary ammonium compounds such as tetraalkylammonium compounds.

Anions used in said conductive salt are preferably inorganic anions such as hexafluorophosphate, tetrafluoroborate, triflate, hexafluoroarsenate, hexafluoroantimonate, tetrafluoroaluminate, tetrafluoroindate, perchlorate, bis(oxalato)borate, tetrachloroaluminate, tetrachlorogallate, but also organic anions, for example $N(CF_3SO_2)_2^-$, $CF_3SO_3^-$, alkoxides, for example tert-butoxide or i-propoxide, but also halides such as fluoride, chloride, bromide and iodide.

The invention is to be illustrated in detail hereinafter by the working examples for preparation and use shown in the drawings.

The drawings show:

FIG. 1: Cyclic voltammogram (14 cycles) of an electrode produced according to Example 4.

Figure 2:
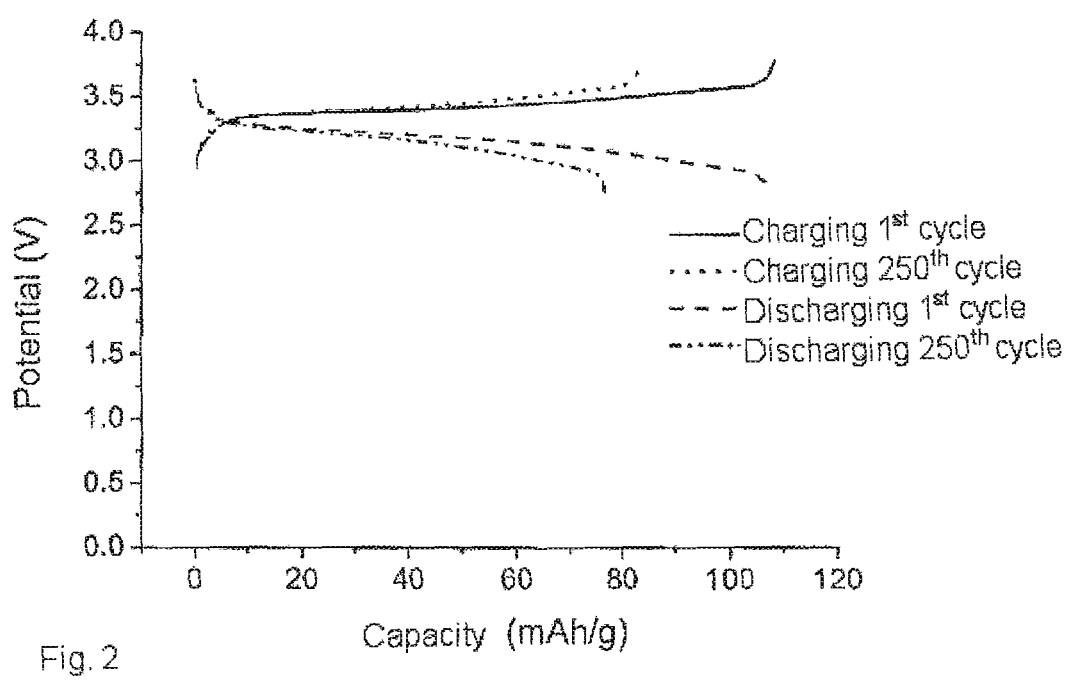

FIG. 2 Charge/discharge curves of the first and two hundred and fiftieth charging/discharging cycle of a secondary battery produced according to Example 5.

Figure 3:
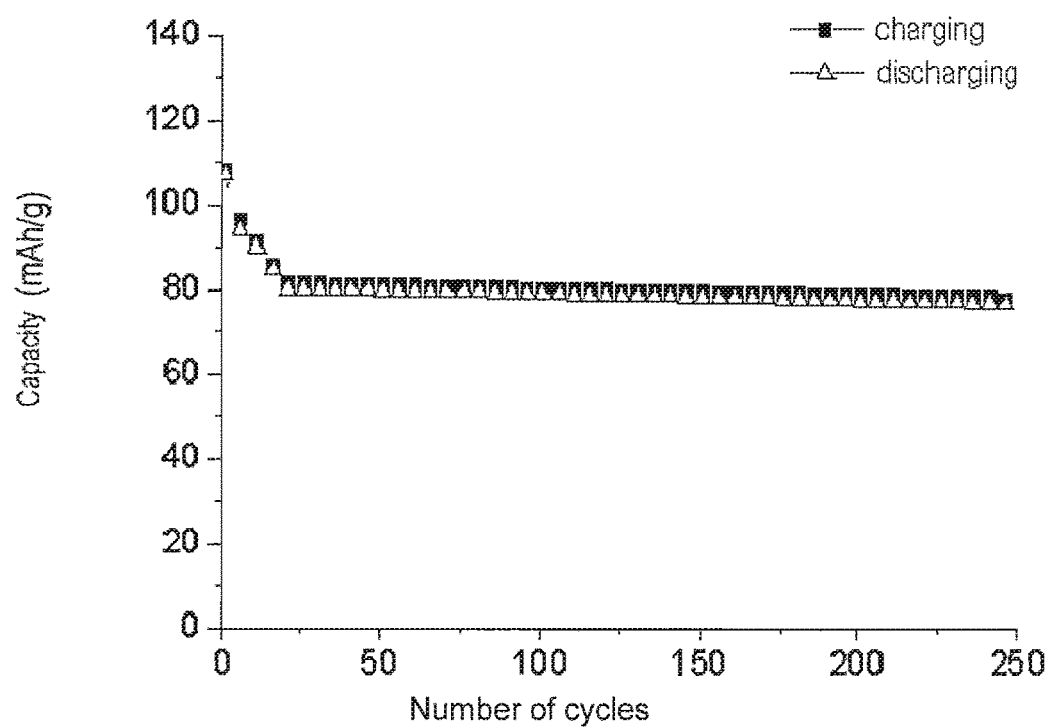

FIG. 3: Charging/discharging behaviour of these condary battery produced according to Example 5.

Figure 4:
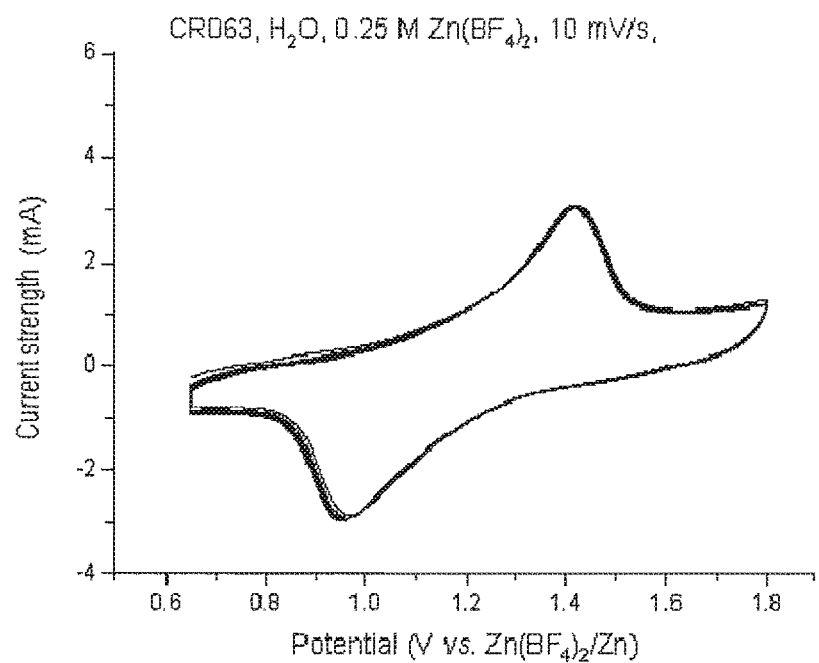

FIG. 4: Cyclic voltammogramm (20 cycles) of an electrode produced according to Example 9.

Figure 5:
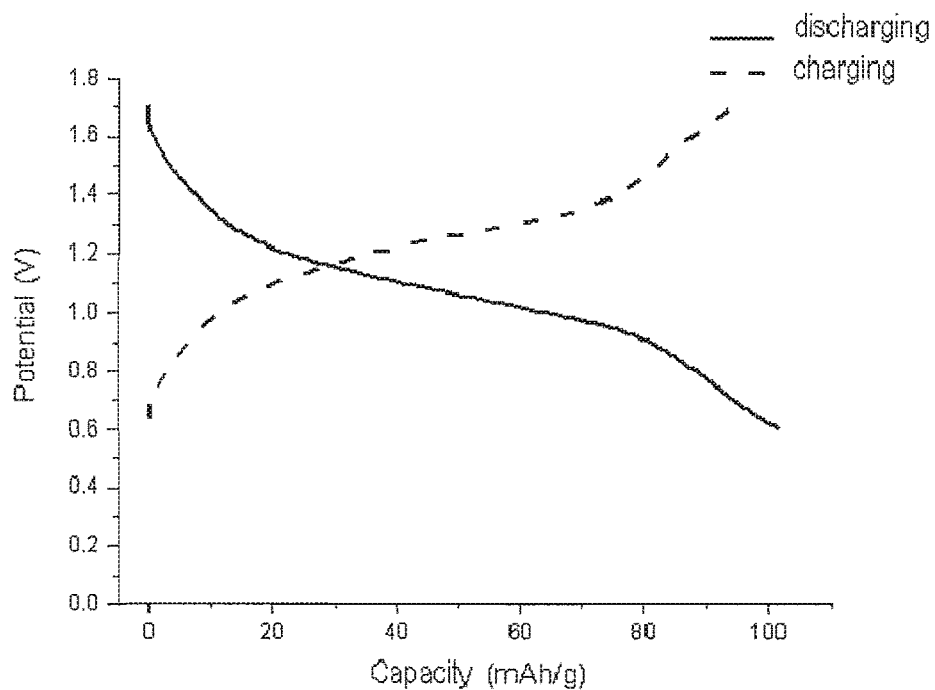

FIG. 5: Charging/discharging behaviour of these condary battery produced according to Example 10.

Figure 6:
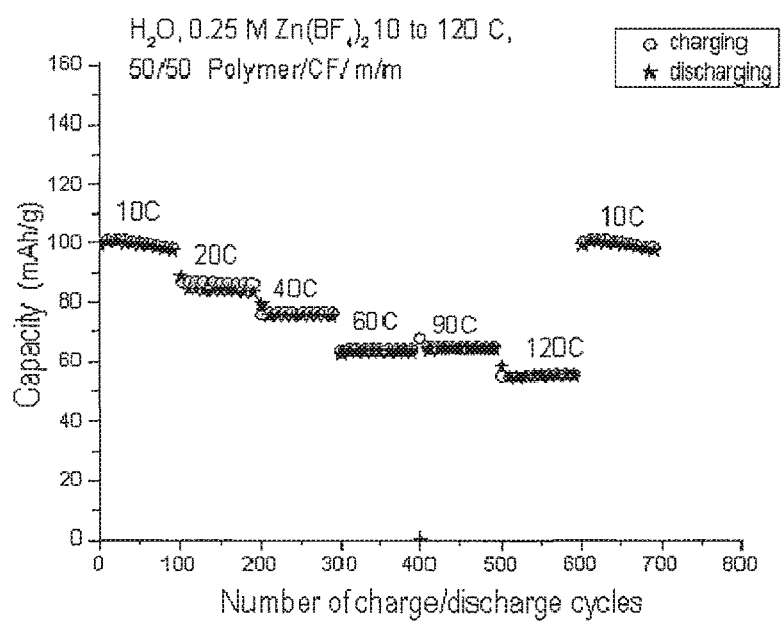

FIG. 6 Charging/discharging behaviour of these condary zinc-organic battery at different charge rates (10 C=full charging in 6 minutes; 20 C=full charging in 3 minutes; 40 C=full charging in 1 minute, 30 seconds; 60 C=full charging in 1 minute; 90 C=full charging in 45 seconds; 120 C=full charging in 30 seconds) produced according to Example 10.

$^1$H and $^{13}$C NMR spectra were recorded with a Bruker AC 300 (300 MHz) spectrometer at 298 K. Elemental analyses were conducted with a Vario ELIII-Elementar Euro instrument and an EA-HekaTech instrument. For cyclic voltammetry and galvanostatic experiments, a Biologic VMP 3 potentiostat was available. Size exclusion chromatography was conducted on an Agilent 1200 series system (degasser: PSS, pump: G1310A, autosampler: G1329A, oven: Techlab, DAD detector: G1315D, RI detector: G1362A, eluent: DMAc+0.21% LiCl, 1 ml/min, temperature: 40° C., column: PSS GRAM guard/1000/30 Å).

Scheme 17:

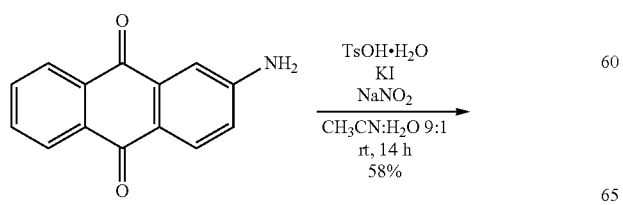

-continued

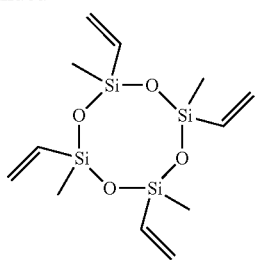

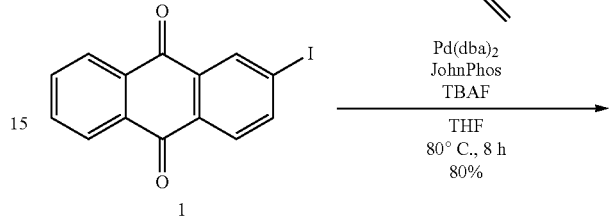

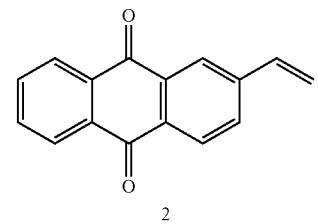

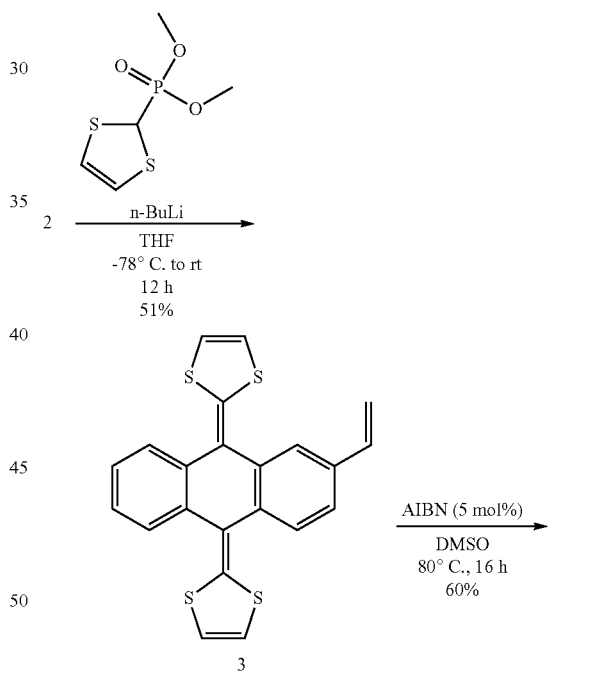

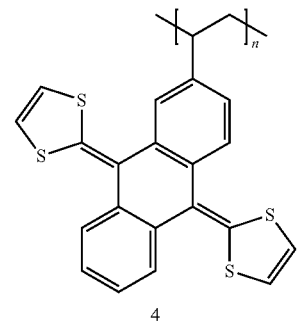

EXAMPLE 1

Synthesis of 2-vinylanthraquinone (2 in the above Scheme 17)

2-Iodoanthraquinone (1.74 g, 5.22 mmol), bis(dibenzylideneacetone)palladium(0) (0.060 g, 0.104 mmol) and biphenyl-2-yidi-tert-butylphosphine (0.062 g, 0.209 mmol) are dissolved in a 0.3 M solution of tetrabutylammonium fluoride in tetrahydrofuran. The solution is purged with argon, and 2,4,6,8-tetramethyl-2,4,6,8-tetravinyl-1,3,5,7,2,4,6,8-tetraoxatetrasilocane (0.902 ml, 2.61 mmol) is added dropwise. The mixture is stirred at 80° C. under an argon atmosphere for eight hours. The reaction mixture is cooled to room temperature and added to 250 ml of ethanol. The precipitate is filtered off and washed twice with n-hexane. After drying under reduced pressure, almost pure 2-vinylanthraquinone (2) (1.175 g, 5.02 mmol, 96%) is obtained as a yellowish solid, the purity of which is sufficient for the next reaction step.

Anal. Calcd for $C_{16}H_{10}O_2$: C, 81.90; H, 4.30. Found: C, 81.85; H, 4.31. $^1$H NMR, (CDCl$_3$, 300 MHz, ppm): δ 5.54 (d, 1H), 6.05 (d, 1H), 6.87 (dd, 1H), 7.80 (m, 3H), 8.32 (m, 4H). $^{13}$C NMR (CDCl$_3$, 75 MHz, ppm): δ 183.2, 182.6, 143.2, 135.4, 134.1, 134.0, 133.8, 133.6, 133.5, 132.5, 131.4, 128.3, 127.8, 127.2, 124.8, 118.4.

EXAMPLE 2

Synthesis of 2,2'-(2-vinylanthracene-9,10-diylidene)bis(1,3-dithiol) (3 in Scheme 17)

Dimethyl-1,3-dithiol-2-yl phosphonate (733 mg, 3.45 mmol) is dissolved in 10 ml of tetrahydrofuran under an argon atmosphere, and the reaction mixture is cooled down to −78° C. A 2.5 M solution of n-butyllithiutn in n-hexane (1.5 ml 3.75 mmol) is added dropwise to the reaction mixture within five minutes. The reaction mixture is stirred at −78° C. for two hours. Thereafter, a solution of 2-vinylanthraquinone (352 mg, 1.50 mmol) in 11.5 ml of tetrahydrofuran is added dropwise at −78° C. After one hour at −78° C., the reaction mixture is stirred at room temperature for a further four hours. 50 ml of ethyl acetate are added to the reaction mixture, and the mixture is extracted twice with water (35 ml) and once with brine (20 ml). The organic phase is dried over magnesium sulphate, filtered and concentrated under reduced pressure. The resultant crude product is purified by means of column chromatography (silica gel; n-hexane/toluene, 1/1). This gives 700 mg (2.12 mmol, 51%) (3) as a yellow powder. Anal. calcd for C2214.10N4: C, 64.99; H, 3.47, S, 31.54. Found: C, 64.81; H, 3.58, S, 30.95. 1H NMR (CD2Cl2, 300 MHz, ppm): δ 7.78 (d, 1H), δ 7.74-7.69 (m, 2H), δ 7.67 (s, 1H), δ 7.38 (d, 1H), δ 7.36 (m, 2H), δ 6.81 (dd, 1H), δ 6.39 (s, 2H), δ 6.38 (s, 1H), δ 5.84 (d, 1H), δ 5.33 (d, 1H). ESI-MS, m/z 406.00 [M+].

EXAMPLE 3

Synthesis of poly(2,2'-(2-vinylanthracene-9,10-diylidene)bis(1,3-dithiol)) (4 in Scheme 17)

50 mg of 2,2'-(2-vinylanthracene-9,10-diylidene)bis(1,3-dithiol) (3) are dissolved in 0.25 ml of dimethyl sulphoxide, and 1.01 mg of AIBN (0.0062 mmol, 5 mol %) are added. The reaction mixture is degassed with argon for five minutes and stirred at 80° C. for 18 hours. Thereafter, the reaction solution is added to 50 ml of dichloromethane, in order to precipitate the product. This forms 30 mg of poly(2,2'-(2-vinylanthracene-9,10-diylidene)bis(1,3-dithiol) (4) as an orange solid.

Anal. Calcd for $C_{22}H_{10}N_4$: C, 80.00; H, 3.10, N, 16.90. Found: C, 79.96; H, 3.13, N, 16.95. $^1$H NMR (DMF-d$_7$, 300 MHz, ppm): δ 8.83 to 7.48 (br, 7H), 2.62 to 1.31 (br, 3H). SEC: $M_n$ 6.02×10$^3$ g/mol (PS standard), PDI: 1.66.

EXAMPLE 4

Production of an Electrode with poly(2,2'-(2-vinylanthracene-9,10-diylidene)bis(1,3-dithiol)) (4 in Scheme 17), cf. FIG. 1

A solution consisting of poly(2,2'-(2-vinylanthracene-9,10-diylidene)bis(1,3-dithiol)) (4) in NMP (N-methyl-2-pyrrolidone) (10 mg/ml) was added to carbon fibres (VGCF; Showa-Denko) as conductivity additive and poly(vinylidene fluoride) (PVDF; Sigma Aldrich) as binder additive (ratio: 10/80/10 v/m/m), These materials were mixed in a mortar for ten minutes, and the resulting paste was applied to an aluminium foil using a coating blade method (thickness: 0.015 mm, MTI Corporation). The electrode is dried at 100° C. for 24 hours.

The electrode is dipped into an electrolyte solution (0.1 M LiClO$_4$ in 1,2-di-methoxy-ethane/propylene carbonate 4/1). For the cyclic voltammetry measurement, a half-cell consisting of said electrode as working electrode and an Ag/AgNO$_3$ electrode as reference electrode, and also a platinum mesh as counterelectrode, is constructed (FIG. 1).

The cyclic voltammogram shows a stable redox reaction at −0.12 V.

EXAMPLE 5

Production of an Li Polymer Battery

The electrode described in Example 4 is introduced into a secondary battery (Li polymer battery) under an argon atmosphere. The electrolyte used is a 0.1 M solution of LiClO$_4$ in 1,2-di-methoxy-ethane/propylene carbonate 4/1; the counterelectrode used is a piece of elemental lithium. The two electrodes are separated from one another by these parator (a porous polypropylene membrane, Celgard). The battery shows a charge plateau at 3.4 V and a discharge plateau at 3.2 V (FIG. 2).

In the first charge/discharge cycle, the battery shows a capacity of 108 mAh/g (82% of the the oretically possible capacity); after 500 charge/discharge cycles, the battery shows a capacity of 82 mAh/g (FIG. 3) at an average coulomb efficiency of 99%.

Scheme 18 shows the schematic representation of the synthesis of poly(2,2'-(2-ethynylanthracene-9,10-diylidene)bis(1,3-dithiol)):

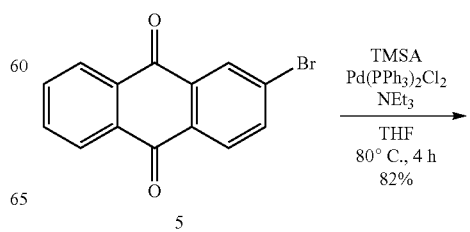

5

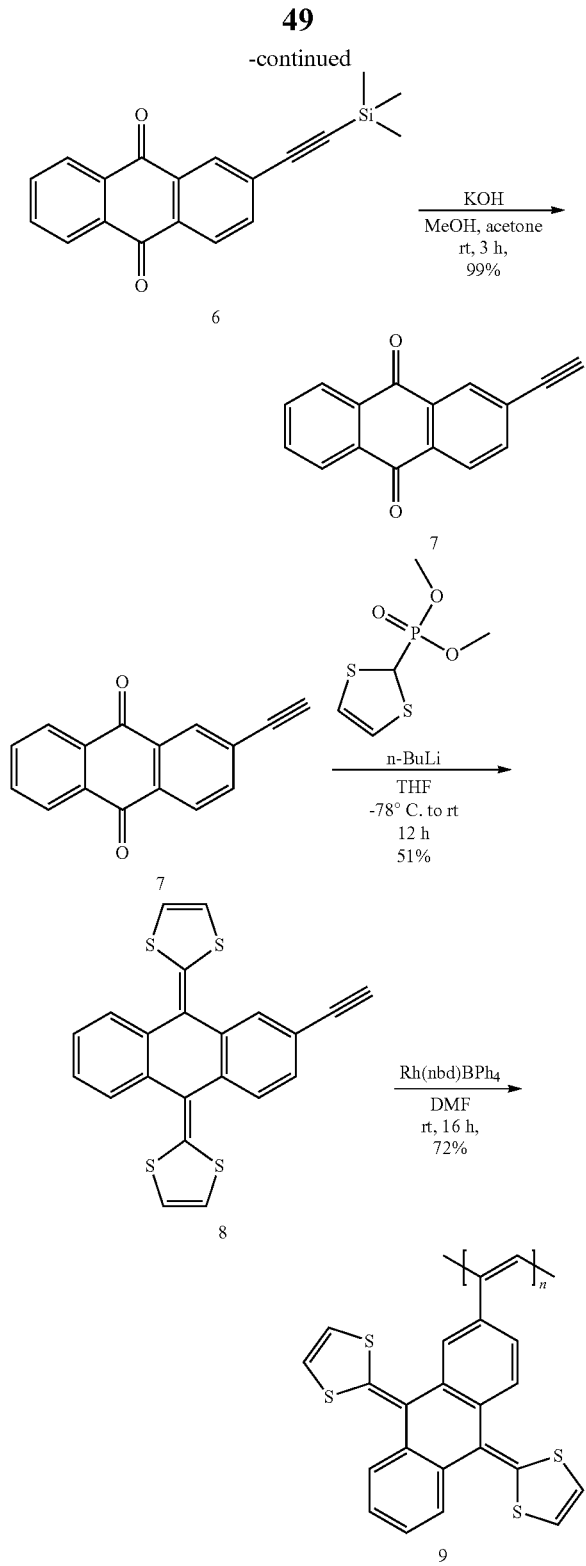

EXAMPLE 6

Synthesis of 2-ethynylanthraquinone (7 in Scheme 18)

2-Bromoanthraquinone (5 in Scheme 18; 1.00 g, 3.5 mmol), copper(I) iodide (0.012 mg, 0.007 mmol) and bis (triphenylphosphine)palladium(II) dichloride (0.042 g, 0.035 mmol) are dissolved in a 1/1 v/v mixture of tetrahydrofuran and triethylamine (11 ml). The solution is purged with argon, and trimethylsilylacetylene (0.54 ml, 3.8 mmol) is added dropwise. The mixture is stirred at 80° C. for six hours under an argon atmosphere. The reaction mixture is cooled to room temperature and 50 ml of chloroform are added. The solution is washed once with 50 ml of saturated aqueous ammonium chloride solution, once with 50 ml of water and once with 50 ml of saturated aqueous sodium chloride solution, dried over magnesium sulphate, filtered and concentrated to dryness under reduced pressure. The crude product is purified by column chromatography (chloroform/n-hexane 5/1), The 2-((trimethylsilypethynyl)anthraquinone obtained (800 mg, 2.64 mmol) is dissolved in 25 ml of an acetone/methanol solution in a ratio of 2/1. Added to this solution is sodium hydroxide (105.2 mg, 2.64 mmol). The reaction mixture is stirred at room temperature for three hours, diluted with 50 ml of chloroform and washed once with 50 ml of saturated aqueous ammonium chloride solution, once with 50 ml of water and once with 50 ml of saturated aqueous sodium chloride solution, dried over magnesium sulphate, filtered and concentrated to dryness under reduced pressure the crude product is purified by column chromatography (chloroform/n-hexane 5/1), This gave 682 mg of 2-ethynylanthraquinone (7 in Scheme 18) as brown crystals.

Anal. calcd for $C_{16}H_8O_2$: C, 82.8; H, 3.5%. Found: C, 82.7; H, 3.3%. $^1$H NMR (CDCl$_3$, 300 MHz, ppm, TMS): d 8.32 (Ph, 4H), 7.83 (Ph, 3H), 3.37 (CH, 1H). $^{13}$C NMR (CDCl$_3$, 300 MHz, ppm, TMS): d 182.8, 137.5, 134.8, 134.7, 133.9, 133.8, 133.3, 131.3, 128.7, 127.8, 127.5, 82.4, 82.3. MS (m/z) calcd for M$^+$ 232.1. Found: 233.1.

EXAMPLE 7

Synthesis of 2,2'-(2-Ethynylanthracene-9,10-diylidene)bis(1,3-dithiol) (8 in Scheme 18)

Dimethyl 1,3-dithiol-2-ylphosphonate (823 mg, 3.2 mmol) is dissolved in 5 ml of tetrahydrofuran under an argon atmosphere and the reaction mixture is cooled to −78° C. A 2.5 M solution of n-butyllithium in n-hexane (1.5 ml, 3.75 mmol) is added dropwise to the reaction mixture over the course of five minutes. The reaction mixture is stirred at −78° C. for two hours. Thereafter a solution of 2-ethynylanthraquinone (7 in Scheme 18; 352 mg, 1.50 mmol) in 11.5 ml of tetrahydrofuran is added dropwise at −78° C., After an hour at −78° C., the reaction mixture is stirred at room temperature for four hours more. The reaction mixture is admixed with 50 ml of chloroform, and the mixture is extracted twice with water (35 ml) and once with saturated aqueous sodium chloride solution (20 ml). The organic phase is dried over magnesium sulphate, filtered and concentrated under reduced pressure. The crude product obtained is purified by column chromatography (silica gel n-hexaneltoluene, 1/1), This gives 418 mg (1.03 mmol, 69%) of product (8 in Scheme 18) as a yellow solid. Anal. Calcd for C22H$_{12}$S$_4$: C, 65.31; H, 2.99, S, 31.70. Found: C, 65.20; H, 2.90, S, 31.62.

EXAMPLE 8

Synthesis of poly(2,2'(2-ethynylanthracene-9,10-diylidene)bis(1,3-dithiol) (9 in Scheme 18)

Under argon, a solution of 50 mg of 2,2'-(2-ethynylanthracene-9,10-diylidene)bis(1,3-dithiol) (8 in Scheme 18) in 0.25 ml of N,N-dimethylformamide is admixed with a solution of 1.49 mg of bicyclo[2.2.1]hepta-2,5-diene-rhalium(I) chloride dimer in 0.1 ml of N,N-dimethylformamide. The reaction solution is stirred at room temperature for 18 hours. Thereafter the reaction solution is added to 50 ml of acetonitrile in order to precipitate the product. This procedure gives rise to 40 mg of poly-2,2'-(2-ethynylanthracene-9,10-diylidene)bis(1,3-dithiol) (9 in Scheme 18) as an orange solid.

Anal. Calcd for $C_{22}H_{12}S_4$: C, 65.31; H, 2.99, S, 31.70. Found: C, 65.29; H, 2.80, S, 31.52. SEC: $M_n$ 8.92×10$^3$ g/mol (PS standard), PDI: 1.84.

EXAMPLE 9

Production of an Electrode with poly(2,2'-(2-ethynylanthracene-9,10-diylidene)bis dithiol))

A solution consisting of poly(2,2'(2-ethynylanthracene-9,10-diyhdene)bis(1,3-dithiol)) (9 in Scheme 18) in NMP (N-methyl-2-pyrrolidone) (5 mg/nil) was added to carbon fibres (MWCNT, Sigma-Aldrich) as conductivity additive (ratio: polymer/conductivity additive 50/50 m/m). These materials were mixed in a mortar for ten minutes, and the resulting paste was applied to a graphite foil using a coating blade method (thickness: 0.254 mm, Alfa Aesar), The electrode is dried at 100° C. for 24 hours.

The electrode is dipped into an electrolyte solution (2 M $Zn(BF_4)_2$ in water). For the cyclic voltammetry measurement, a half-cell consisting of said electrode as working electrode and an Ag/AgCl electrode as reference electrode, and also a zinc foil as counterelectrode, is constructed.

The cyclic voltammogram (FIG. 4) shows a stable redox reaction between 0.8 and 1.6 V.

EXAMPLE 10

Production of a Zinc Polymer Battery

The electrode described in Example 9 is introduced into a secondary battery (Zn polymer battery). In this battery, zinc metal functions as the anode and the polymer composite electrode as cathode. The electrolyte used is a 2 M solution of $Zn(BF_4)_2$ in water; the counterelectrode used is a piece of elemental zinc foil. The two electrodes are separated from one another by the electrolytes (distance about 3 mm). The battery shows a charge plateau at 1.2 V and a discharge plateau at 1.1 V (FIG. 5).

In the first charge/discharge cycle, at a rate of 10 C (=full charging in 6 minutes), the battery shows a capacity of 100 mAh/g (78% of the the oretically possible capacity); after 100 charge/discharge cycles, the battery shows a capacity of 95 mAh/g (FIG. 6) at an average coulomb efficiency of 99% (coulomb efficiency=ratio of the charge withdrawn from the battery during a charge/discharge cycle to the charge supplied to the battery during the same charge/discharge cycle). The battery can be charged at up to 120 C. At a charging rate of 120 C. (full charging in 30 seconds), the battery shows a capacity of 55 mAh/g (40% activity of material).

The invention claimed is:
1. A 9,10-Bis(1,3-dithiol-2-ylidene)-9,10-dihydroanthracene polymer, comprising:
an oligomeric or polymeric compound having a structure of the formula I

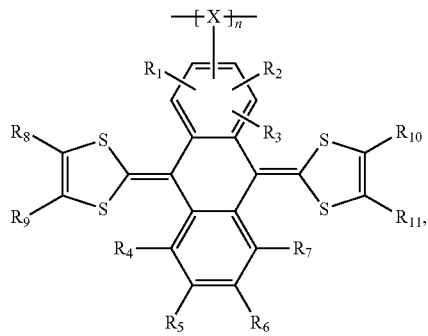

wherein
$R_1$ to $R_7$ are each independently hydrogen atoms, alkyl groups, alkenyl groups, alkynyl groups, alkoxy groups, alkylthio groups, haloalkyl groups, haloalkoxy groups, cycloalkyl groups, cycloalkoxy groups, aryl groups, heteroaryl groups, aryloxy groups, aralkyl groups, carboxylic acid groups, sulphonic acid groups, amino groups, monoalkylamino groups, dialkylamino groups, nitro groups, cyano groups, hydroxyl groups, alkylcarbonyl groups, alkenylcarbonyl groups, alkynylcarbonyl groups, carboxylic ester groups, carboxamide groups, sulphonic ester groups, thiol groups, halogen atoms or a combination of these groups or atoms,
$R_8$ to $R_{11}$ are each independently hydrogen atoms, alkyl groups, alkenyl groups, alkynyl groups, alkoxy groups, alkylthio groups, haloalkyl groups, haloalkoxy groups, cycloalkyl groups, cycloalkoxy groups, aryl groups, heteroaryl groups, aryloxy groups, aralkyl groups, amino groups, monoalkylamino groups, dialkylamino groups, nitro groups, cyano groups, hydroxyl groups, alkylcarbonyl groups, alkenylcarbonyl groups, alkynylcarbonyl groups, carboxylic ester groups, carboxamide groups, sulphonic ester groups, thiol groups, halogen atoms or a combination of these groups or atoms,
the $R_8$ and $R_9$ substituents, the $R_{10}$ and $R_{11}$ substituents, or both the $R_8$ and $R_9$ substituents and the $R_{10}$ and $R_{11}$ substituents form an aromatic, heteroaromatic or non-aromatic ring comprising five to seven atoms,
X is an organic group obtained by a polymerization reaction of at least one functionality selected from the group consisting of an organic double bond, an organic triple bond, an oxirane and an aziridine, and
n is an integer greater than or equal to 2.
2. The 9,10-Bis(1,3-dithiol-2-ylidene)-9,10-dihydroanthracene polymer according to claim 1, wherein X is an organic group having a structure of one of the formulas II-XIV:

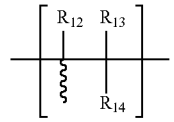

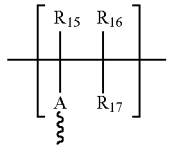

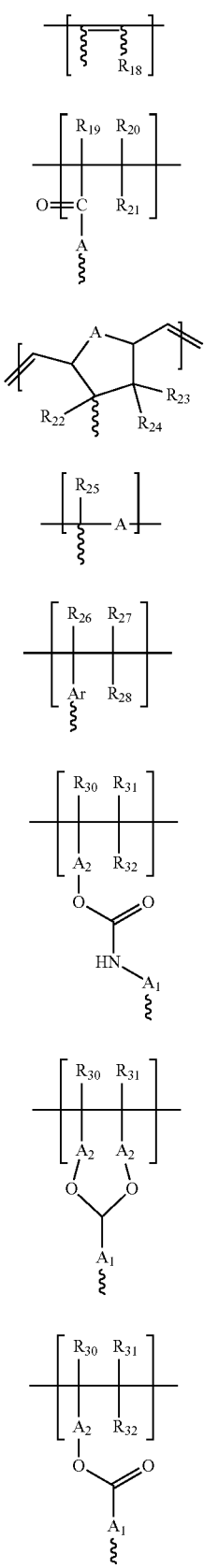

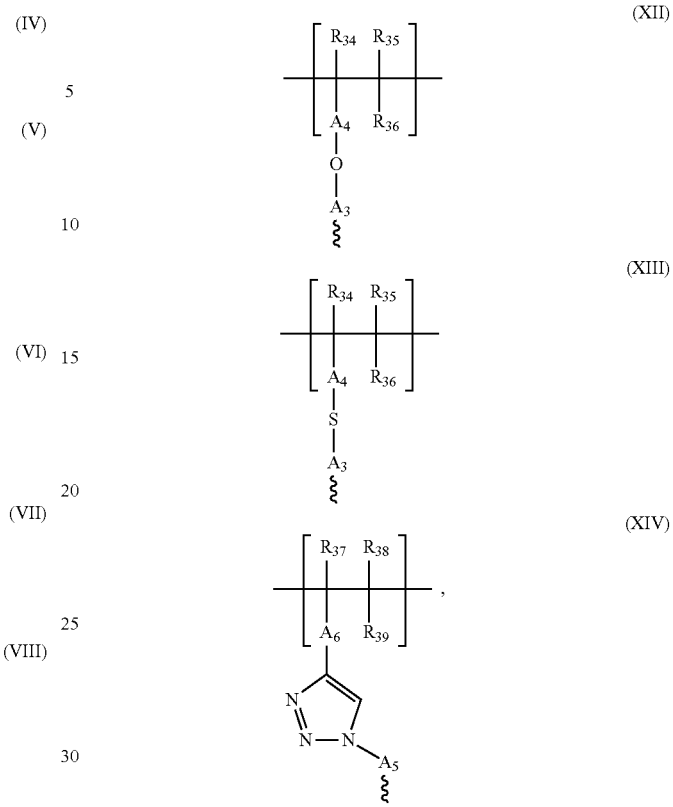

wherein

R$_{12}$ to R$_{28}$ are each independently hydrogen atoms, alkyl groups, alkenyl groups, alkynyl groups, alkoxy groups, alkylthio groups, haloalkyl groups, haloalkoxy groups, cycloalkyl groups, cycloalkoxy groups, aryl groups, heteroaryl groups, aryloxy groups, aralkyl groups, carboxylic acid groups, sulphonic acid groups, amino groups, monoalkylamino groups, dialkylamino groups, nitro groups, cyano groups, hydroxyl groups, alkylcarbonyl groups, alkenylcarbonyl groups, alkynylcarbonyl groups, carboxylic ester groups, carboxamide groups, sulphonic ester groups, thiol groups, halogen atoms or a combination of these groups or atoms, R$_{30}$ to R$_{32}$ are each independently hydrogen atoms, alkyl groups, alkenyl groups, alkynyl groups, alkoxy groups, alkylthio groups, haloalkyl groups, haloalkoxy groups, cycloalkyl groups, cycloalkoxy groups, aryl groups, heteroaryl groups, aryloxy groups, aralkyl groups, carboxylic acid groups, sulphonic acid groups, amino groups, monoalkylamino groups, dialkylamino groups, nitro groups, cyano groups, hydroxyl groups, alkylcarbonyl groups, alkenylcarbonyl groups, alkynylcarbonyl groups, carboxylic ester groups, carboxamide groups, sulphonic ester groups, thiol groups, halogen atoms or a combination of these groups or atoms, R$_{34}$ to R$_{36}$ are each independently hydrogen atoms, alkyl groups, alkenyl groups, alkynyl groups, alkoxy groups, alkylthio groups, haloalkyl groups, haloalkoxy groups, cycloalkyl groups, cycloalkoxy groups, aryl groups, heteroaryl groups, aryloxy groups, aralkyl groups, carboxylic acid groups, sulphonic acid groups, amino groups, monoalkylamino groups, dialkylamino groups, nitro groups, cyano groups, alkylcarbonyl groups, alkenylcarbonyl groups, alkynylcarbonyl groups, carboxylic ester groups, carboxamide groups, sulphonic ester groups, halogen atoms or a combination of these groups or atoms, $R_{37}$ to $R_{39}$ are each independently hydrogen atoms, alkyl groups, alkenyl groups, alkoxy groups, alkylthio groups, haloalkyl groups, haloalkoxy groups, cycloalkyl groups, cycloalkoxy groups, aryl groups, heteroaryl groups, aryloxy groups, aralkyl groups, carboxylic acid groups, sulphonic acid groups, amino groups, monoalkylamino groups, dialkylamino groups, nitro groups, cyano groups, hydroxyl groups, alkylcarbonyl groups, alkenylcarbonyl groups, alkynylcarbonyl groups, carboxylic ester groups, carboxamide groups, sulphonic ester groups, thiol groups, halogen atoms or a combination of these groups or atoms, A is an oxygen atom, a sulphur atom or an —N($R_{33}$)— group, wherein $R_{33}$ is a hydrogen atom, an alkyl group, an alkenyl group, an alkynyl group, an alkoxy group, an alkylthio group, a haloalkyl group, a haloalkoxy group, a cycloalkyl group, a cycloalkoxy group, an aryl group, a heteroaryl group, an aryloxy group, an aralkyl group, a carboxylic acid group, a sulphonic acid group, a nitro group, an alkylcarbonyl group, an alkenylcarbonyl group, an alkynylcarbonyl group, a carboxylic ester group, a carboxamide group, or a sulphonic ester group, $A_1$ and $A_2$ are each independently a covalent bond, an alkyl group, an alkenyl group, an alkynyl group, an alkoxy group, an alkylthio group, a haloalkyl group, a haloalkoxy group, a cycloalkyl group, a cycloalkoxy group, an aryl group, a heteroaryl group, an aryloxy group, an aralkyl group, a monoalkylamino group, a dialkylamino group, an alkylcarbonyl group, an alkenylcarbonyl group, an alkynylcarbonyl group, a carboxylic ester group, a carboxamide group, or a sulphonic ester group, $A_3$ and $A_4$ are each independently a covalent bond, an alkyl group, an alkenyl group, an alkynyl group, an alkoxy group, an alkylthio group, a cycloalkyl group, a cycloalkoxy group, an aryl group, a heteroaryl group, an aryloxy group, an aralkyl group, a dialkylamino group, an alkylcarbonyl group, an alkenylcarbonyl group, an alkynylcarbonyl group, a carboxylic ester group, a carboxamide group, or a sulphonic ester group, $A_5$ and $A_6$ are each independently a covalent bond, an alkyl group, an alkenyl group, an alkoxy group, an alkylthio group, a haloalkyl group, a haloalkoxy group, a cycloalkyl group, a cycloalkoxy group, an aryl group, a heteroaryl group, an aryloxy group, an aralkyl group, a monoalkylamino group, a dialkylamino group, an alkylcarbonyl group, an alkenylcarbonyl group, an alkynylcarbonyl group, a carboxylic ester group, a carboxamide group, or a sulphonic ester group, Ar is an independently substituted cycloalkyl group, cycloalkoxy group, aryl group, heteroaryl group, aryloxy group, or aralkyl group.

3. An electrical charge storage device, comprising:
an active electrode material, the active electrode material comprising the 9,10-bis(1,3-dithiol-2-ylidene)-9,10-dihydroanthracene polymer according to claim 1.

4. The electrical charge storage device according to claim 3, wherein the active electrode material comprising the 9,10-bis(1,3-dithiol-2-ylidene)-9,10-dihydroanthracene polymer is present as a full or partial surface coating of electrode elements of the electrical charge storage device.

5. An electrode slurry, comprising:
the 9,10-bis(1,3-dithiol-2-ylidene)-9,10-dihydroanthracene polymer according to claim 1.

6. The 9,10-Bis(1,3-dithiol-2-ylidene)-9,10-dihydroanthracene polymer according to claim 1, wherein at least five of the $R_1$ to $R_7$ substituents are hydrogen atoms and zero to two $R_1$ to $R_7$ substituents are non-hydrogen atoms.

7. The 9,10-Bis(1,3-dithiol-2-ylidene)-9,10-dihydroanthracene polymer according to claim 6, wherein the non-hydrogen atoms if present are each independently halogen atoms, alkyl groups, alkoxy groups, cyano groups, or nitro groups.

8. The 9,10-Bis(1,3-dithiol-2-ylidene)-9,10-dihydroanthracene polymer according to claim 1, wherein the $R_8$ and $R_9$ substituents, the $R_{10}$ and $R_{11}$ substituents, or both the $R_8$ and $R_9$ substituents and the $R_{10}$ and $R_{11}$ substituents form a nonaromatic ring comprising at least one functionality selected from the group consisting of alkyl groups, alkenyl groups, alkynyl groups, alkoxy groups, alkylthio groups, haloalkyl groups, haloalkoxy groups, cycloalkyl groups, cycloalkoxy groups, aryl groups, heteroaryl groups, aryloxy groups, aralkyl groups, amino groups, monoalkylamino groups, dialkylamino groups, alkylcarbonyl groups, alkenylcarbonyl groups, alkynylcarbonyl groups, carboxylic ester groups, carboxamide groups, and sulphonic ester groups.

9. The 9,10-Bis(1,3-dithiol-2-ylidene)-9,10-dihydroanthracene polymer according to claim 1, wherein at least one of the $R_8$ to $R_{11}$ substituents is an alkyl group, an alkythio group, or a thiol group.

10. The 9,10-Bis(1,3-dithiol-2-ylidene)-9,10-dihydroanthracene polymer according to claim 1, wherein at least one of the $R_8$ to $R_{11}$ substituents is a methyl group, an ethyl group, methylthio group, or an ethylthio group.

11. The 9,10-Bis(1,3-dithiol-2-ylidene)-9,10-dihydroanthracene polymer according to claim 2, wherein the $R_{18}$ substituent if present, the $R_{25}$ substituent if present, or both are a hydrogen atom.

12. The 9,10-Bis(1,3-dithiol-2-ylidene)-9,10-dihydroanthracene polymer according to claim 2, wherein at least one of the following parameters is met;
at least two of the $R_{12}$ to $R_{14}$ substituents if present are hydrogen atoms and zero to one of the $R_{12}$ to $R_{14}$ substituents if present are non-hydrogen atoms,
at least two of the $R_{15}$ to $R_{17}$ substituents if present are hydrogen atoms and zero to one of the $R_{15}$ to $R_{17}$ substituents if present are non-hydrogen atoms,
at least two of the $R_{19}$ to $R_{21}$ substituents if present are hydrogen atoms and zero to one of the $R_{19}$ to $R_{21}$ substituents if present are non-hydrogen atoms,
at least two of the $R_{22}$ to $R_{24}$ substituents if present are hydrogen atoms and zero to one of the $R_{22}$ to $R_{24}$ substituents if present are non-hydrogen atoms, or
at least two of the $R_{26}$ to $R_{28}$ substituents if present are hydrogen atoms and zero to one of the $R_{26}$ to $R_{28}$ substituents if present are non-hydrogen atoms.

13. The 9,10-Bis(1,3-dithiol-2-ylidene)-9,10-dihydroanthracene polymer according to claim 12, wherein the non-hydrogen atoms if present are each independently halogen atoms, alkyl groups, alkoxy groups, cyano groups, or nitro groups.

14. The 9,10-Bis(1,3-dithiol-2-ylidene)-9,10-dihydroanthracene polymer according to claim 2, wherein at least one of the following parameters is met;
at least two of the $R_{30}$ to $R_{32}$ substituents if present are hydrogen atoms and zero to one of the $R_{30}$ to $R_{32}$ substituents if present are non-hydrogen atoms, at least two of the $R_{34}$ to $R_{36}$ substituents if present are hydrogen atoms and zero to one of the $R_{34}$ to $R_{36}$ substituents if present are non-hydrogen atoms, or at least two of the $R_{37}$ to $R_{39}$ substituents if present are hydrogen atoms and zero to one of the $R_{37}$ to $R_{39}$ substituents if present are non-hydrogen atoms.

15. The 9,10-Bis(1,3-dithiol-2-ylidene)-9,10-dihydroanthracene polymer according to claim 14, wherein the non-hydrogen atoms if present are each independently halogen atoms, alkyl groups, alkoxy groups, cyano groups, or nitro groups.

16. The 9,10-Bis(1,3-dithiol-2-ylidene)-9,10-dihydroanthracene polymer according to claim 2, wherein A if present is an oxygen atom.

17. The 9,10-Bis(1,3-dithiol-2-ylidene)-9,10-dihydroanthracene polymer according to claim 2, wherein the $A_1$ substituent if present, the $A_2$ substituent if present, the $A_3$ substituent if present, the $A_4$ substituent if present, the $A_5$ substituent if present, and the $A_6$ substituent if present are each independently a covalent bond or an alkyl group.

18. The electrical charge device according to claim 3, wherein the electrical charge storage device is a secondary battery.

19. The electrical charge device according to claim 4, wherein the electrical charge storage device is a secondary battery.

20. A method of forming an electrode, the method comprising:

providing an electrode slurry comprising the 9,10-Bis(1,3-dithiol-2-ylidene)-9,10-dihydroanthracene polymer according to claim 1;

wherein the electrode comprises an active electrode material, the active electrode material comprising the 9,10-Bis(1,3-dithiol-2-ylidene)-9,10-dihydroanthracene polymer, and wherein the active electrode material is present as a full or partial surface coating of the electrode.

* * * * *